(12) United States Patent
Knaupp et al.

(10) Patent No.: US 11,440,942 B2
(45) Date of Patent: Sep. 13, 2022

(54) COMPLEMENT FACTOR BASED AFFINITY CHROMATOGRAPHY

(71) Applicant: Hoffmann-La Roche Inc., Little Falls, NJ (US)

(72) Inventors: Alexander Knaupp, Wackersberg (DE); Laurent Lariviere, Munich (DE); Petra Rueger, Penzberg (DE); Tilman Schlothauer, Penzberg (DE); Stefan Seeber, Sindelsdorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 187 days.

(21) Appl. No.: 16/354,627

(22) Filed: Mar. 15, 2019

(65) Prior Publication Data

US 2020/0002391 A1    Jan. 2, 2020

Related U.S. Application Data

(63) Continuation of application No. PCT/EP2017/073402, filed on Sep. 18, 2017.

(30) Foreign Application Priority Data

Sep. 19, 2016 (EP) .................................... 16189372

(51) Int. Cl.
    C07K 14/47    (2006.01)
    B01D 15/38    (2006.01)
    C07K 1/22     (2006.01)
    C07K 16/18    (2006.01)
    C12N 15/10    (2006.01)

(52) U.S. Cl.
    CPC ........ *C07K 14/472* (2013.01); *B01D 15/3809* (2013.01); *C07K 1/22* (2013.01); *C07K 16/18* (2013.01); *C07K 2317/92* (2013.01); *C07K 2317/94* (2013.01); *C07K 2319/00* (2013.01)

(58) Field of Classification Search
    CPC .. B01D 15/3804; B01D 15/3809; C07K 1/22; C07K 14/472; C07K 16/18; C07K 2317/92; C07K 2317/94; C07K 2319/00; G01N 2333/4716
    See application file for complete search history.

(56) References Cited

U.S. PATENT DOCUMENTS

| 4,676,980 A | 6/1987 | Segal et al. |
| 4,816,567 A | 3/1989 | Cabilly et al. |
| 5,208,020 A | 5/1993 | Chari et al. |

(Continued)

FOREIGN PATENT DOCUMENTS

| CN | 105682740 A | 6/2016 |
| EP | 0 307 434 B1 | 3/1989 |

(Continued)

OTHER PUBLICATIONS

(International Search Report—PCT/EP2017/073402 dated Nov. 8, 2017 dated Oct. 30, 2017).

(Continued)

*Primary Examiner* — Jeremy C Flinders
(74) *Attorney, Agent, or Firm* — Charles Wong

(57) ABSTRACT

Herein is reported a fusion polypeptide according to formula I (TAG-X1-C1qA-X2-C1qB-X3-C1qC-X4), comprising a fragment of SEQ ID NO: 01 (C1qA), a fragment of SEQ ID NO: 03 (C1qB), a fragment of SEQ ID NO: 05 (C1qC) and optionally a tag (TAG).

12 Claims, 18 Drawing Sheets

Specification includes a Sequence Listing.

(56) References Cited

U.S. PATENT DOCUMENTS

| | | |
|---|---|---|
| 5,416,064 A | 5/1995 | Chari et al. |
| 5,500,362 A | 3/1996 | Robinson et al. |
| 5,571,894 A | 11/1996 | Wels et al. |
| 5,587,458 A | 12/1996 | King et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,658,570 A | 8/1997 | Newman et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,877,296 A | 3/1999 | Hamann et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,197,526 B1 | 3/2001 | Yu et al. |
| 6,417,429 B1 | 7/2002 | Hein et al. |
| 6,602,684 B1 | 8/2003 | Umana et al. |
| 6,630,579 B2 | 10/2003 | Chari et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,332,581 B2 | 2/2008 | Presta |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 2002/0164328 A1 | 11/2002 | Shinkawa et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0208586 A1 | 9/2005 | Shen |
| 2005/0266000 A1 | 12/2005 | Bond |
| 2006/0025576 A1 | 2/2006 | Miller et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2015/0329606 A1 | 11/2015 | Thielens et al. |

FOREIGN PATENT DOCUMENTS

| | | |
|---|---|---|
| EP | 0 425 235 A3 | 10/1990 |
| EP | 3042954 | 7/2016 |
| JP | 2004189658 | 7/2004 |
| JP | 2013079272 A | 5/2013 |
| WO | 92/22764 A1 | 12/1992 |
| WO | 93/08829 A1 | 5/1993 |
| WO | 93/16185 A2 | 8/1993 |
| WO | 93/16185 A3 | 8/1993 |
| WO | 1994/11026 | 5/1994 |
| WO | 94/29351 A2 | 12/1994 |
| WO | 97/30087 A1 | 8/1997 |
| WO | 98/58964 A1 | 12/1998 |
| WO | 99/51642 A1 | 10/1999 |
| WO | 00/61739 | 10/2000 |
| WO | 01/29246 A1 | 4/2001 |
| WO | 02/031140 A1 | 4/2002 |
| WO | 03/011878 A2 | 2/2003 |
| WO | 03/084570 A1 | 10/2003 |
| WO | 03/085107 A1 | 10/2003 |
| WO | 2004/056312 A2 | 7/2004 |
| WO | 2005/035586 A1 | 4/2005 |
| WO | 2005/035778 A1 | 4/2005 |
| WO | 2005/053742 A1 | 6/2005 |
| WO | 2005/100402 | 10/2005 |
| WO | 2006/029879 A2 | 7/2006 |
| WO | 2008/077546 A1 | 7/2008 |
| WO | 2009/080251 A1 | 7/2009 |
| WO | 2009/080252 A1 | 7/2009 |
| WO | 2009/080253 A1 | 7/2009 |
| WO | 2009/080254 A1 | 7/2009 |
| WO | 2009/089004 A1 | 7/2009 |
| WO | 2010/048313 | 4/2010 |
| WO | 2010/112193 A1 | 10/2010 |
| WO | 2010/115589 A1 | 10/2010 |
| WO | 2010/136172 A1 | 12/2010 |
| WO | 2010/145792 A1 | 12/2010 |
| WO | 2010/145793 A1 | 12/2010 |
| WO | 2013/120929 A1 | 8/2013 |
| WO | 2015/006504 | 1/2015 |
| WO | 2015/034056 | 3/2015 |

OTHER PUBLICATIONS

Almagro et al., "Humanization of antibodies" Frontiers in Bioscience 13:1619-1633 (Jan. 1, 2008).

Armour et al., "Recombinant human IgG molecules lacking Fcÿ receptor I binding and monocyte triggering activities," Eur. J. Immunol. 1999. 29: 2613-2624.

Assimeh, S., et al., "A Simple Method for the Isolation of the Sub-components of the first Component of the Complement by Affinity Chromatography" J Immunol 113(13):225-234 (Jul. 1, 1974).

Ausubel et al. Current Protocols in Molecular Biology "Percentage of Codon Synonymous Usage and Frequency of Codon Occurrence in Various Organisms" (A1.8-A1.9 (tables)),John Wiley & Sons, Inc., vol. 5:A.1C.1-A.1C.12 ( 1997).

Baca et al., "Antibody humanization using monovalent phage display" J Biol Chem 272(16):10678-10684 ( 1997).

Bally, I., et al., "Expression of recombinant human complement C1q allows identification of the C1r/C1s-binding sites" PNAS 110(21):8650-8655 (May 21, 2013).

Boerner et al., "Production of antigen-specific human monoclonal antibodies from in vitro-primed human splenocytes" J Immunol 147(1):86-95 (Jul. 1, 1991).

Brennan et al., "Preparation of Biospecific Antibodies by Chemical Recombination of Monoclonal Immunoglobulin G1 Fragments" Science 229(4708):81-83 (Jul. 5, 1985).

Brodeur et al. Monoclonal Antibody Production Techniques and Applications New York:Marcel Dekker, Inc.,:51-63 ( 1987).

Brueggemann et al., "Comparison of the effector functions of human immunoglobulins using a matched set of chimeric antibodies" J. Exp. Med. 166:1351-1361 ( 1987).

Brunhouse, R. et al., "Isotypes of IgG comparison of the primary structures of three pairs of isotypes which differ in their ability to activate complement" J Mol Immunol 16:907-917 ( 1979).

Burton, D.R. et al., "The C1q receptor site on immunoglobulin G" Nature 288:338-344 ( 1980).

Burton, "Immunoglobulin G: Functional Sites*" Molecular Immunology 22(3):161-206 ( 1985).

Capel et al., "Heterogeneity of human IgG Fc receptors" Immunomethods 4:25-34 (1994).

(56) References Cited

OTHER PUBLICATIONS

Carter et al., "Humanization of an anti-p185 HER2 antibody for human cancer therapy" P Natl Acad Sci USA 89:4285-4289 (May 1992).
Chari et al., "Immunoconjugates containing novel maytansinoids: Promising anticancer drugs" Cancer Res 52:127-131 ( 1992).
Charlton, "Expression and Isolation of Recombinant Antibody Fragments in E. coli" Methods in Molecular Biology 248:245-254.
Chothia et al., "Canonical structures for the hypervariable regions of immunoglobulins" J Mol Biol 196(4):901-917 ( 1987).
Chowdhury, "Engineering Hot Spots for Affinity Enhancement of Antibodies" Methods in Molecular Biology 207:179-196.
Clackson et al., Nature 352(6336):624-628 (Aug. 15, 1991).
Clynes et al., "Fc receptors are required in passive and active immunity to melanoma" P Natl Acad Sci USA 95(2):652-656 (Jan. 1998).
Cragg et al., "Antibody specificity controls in vivo effector mechanisms of anti-CD20 reagents" Blood 103(7):2738-2743 ( 2004).
Cragg et al., "Complement-mediated lysis by anti-CD20 mAb correlates with segregation into lipid rafts" Blood 101(3):1045-1052 ( 2003).
Cunningham and Wells, "High-resolution epitope mapping of hGH-receptor interactions by alanine-scanning mutagenesis" Science 24: 1081-1085 (Jun. 2, 1989)
Dall'Acqua et al., "Antibody humanization by framework shuffling" Methods 36:43-60 ( 2005).
Davies et al., "Expression of GnTIII in a Recombinant Anti-CD20 CHO Production Cell Line: Expression of Antibodies with Altered Glycoforms Leads to an Increase in ADCC Through Higher Affinity for FcγRIII" Biotechnol Bioeng. 74(4):288-294 ( 2001).
de Hass et al., "Fcγ receptors of phagocytes" J Lab. Clin. Med. 126(4):330-341 ( 1995).
Dubowehik et al., "Doxorubiein Immunoeonjugates Containing Bivalent, Lysosmally-Cleavable Dipeptide Linkages" Bioorg. & Med. Chem. Letters 12:1529-1532 ( 2002).
Duncan and Winter, "The Binding Site for C1q on IgG" Nature 332:738-740 (Apr. 21, 1988).
Ellman et al., "Biosynthetic method for introducing unnatural amino acids site-specifically into proteins" Meth Enzym 202:301-336 ( 1991).
Fellouse et al., "Synthetic antibodies from a four-amino-acid code: A dominant role for tyrosine in antigen recognition" P Natl Acad Sci USA 101(34):12467-12472 (Aug. 24, 2004).
Fraehet, Philippe, et al. Autoimmunity—Pathogenesis, Clinical Aspects and Therapy of Specific Autoimmune Diseases "Chapter 2: Role of C1q in Efferocytosis and Self-Tolerance Links With Autoimmunity" (https://www.intechopen.com/about-intechopen), London, England—UK:IntechOpen.com,:21-51 (Jun. 17, 2015).
G. Köhler et al., "Continuous cultures of fused cells secreting antibody of predefined specificity" Nature 256:495-497 (Aug. 7, 1975).
Gandhi et al., "Anti-p40 antibodies ustekinumab and bnriakinumab: blockade of interleukin-12 and interleukin-23 in the treatment of psonriasis" Semin. Cutan. Med. Surg. 29:48-52 ( 2010).
Gazzano-Santoro, et al., "A non-radioactive complement-dependent cytotoxicity assay for anti-CD20 monoclonal antibody," J Immunol Methods 202(2):163-171 (Mar. 28, 1997).
Gemgross, "Advances in the Production of Human Therapeutic Proteins in Yeasts and Filamentous Fungi," Nat. Biotech. 22:1409-1414 (2004).
Gessner, et al., "The IgG Fc receptor family," Ann Hematol 76 (1998) 231-248.
Ghebrehiwet, Berhane, et al., "Identification of the RAJI Cell Membrane-derived C1q Inhibitor as a Receptor for Human C1q: Purification and Imrnunoehemieal Characterization" J Exp Med 160:1375-1389 (Nov. 14, 1984).
Gibbons, James J., et al., "Temperature-Sensitive Binding of Solid Phase C1q to Aggregated Human Imiviunoglobuling" Acta Biochim ET Biophys 670:146-149 (Jan. 26, 1981).

Graham et al., "Characteristics of a Human Cell Line Transformed by DNA from Human Adenovirus Type 5" J. Gen. Virol. 36(1):59-74 ( 1977).
Griffiths et al., "Human anti-self antibodies with high specificity from phage display libraries" EMBO J 12(2):725-734 ( 1993).
Gruber et al., "Efficient tumor cell lysis mediated by a bispecific single chain antibody : expressed in *Escherichia coli*" J Immunol 152:5368-5374 ( 1994).
Guyer et al., "Immunoglobulin binding by mouse intestinal epithelial cell receptors" J Immunol 117(2):587-593 (Aug. 1976).
Hames, B.D., eds. et al. Nucleic Acid Hybridisation: A Practical Approach Hames, B.D. and Higgins, S.J.,IRL Press/Oxford Univ Press,:1-264 (Dec. 1, 1985).
Hellstrom, et al., "Antitumor effects of L6, an IgG2a antibody that reacts with most human carcinomas," P Natl Acad Sci USA 83:7059-7063 (1986).
Hellstrom, et al., "Strong antitumor activities of IgG3 antibodies to a human melanoma-associated ganglioside," P Natl Acad Sci USA 82:1499-502 (Mar. 1985).
Hermanson, et al. Bioconjugate Techniques "Antibody Modification and Conjugation" San Diego:Academic Press, Inc.,:456 (1996).
Hezareh, et al., "Effector function activities of a panel of mutants of a broadly neutralizing antibody against human immunodeficiency virus type 1." J Virol 75(24):12161-12168 (Dec. 2001).
Hinman et al., "Preparation and characterization of monoclonal antibody conjugates of the calicheamicins: A novel and potent family of antitumor antibiotics" Cancer Res 53:3336-3342 (1993).
Holliger et al., "'Diabodies': Small bivalent and bispecific antibody fragments" P Natl Acad Sci USA 90:6444-6448 (Jul. 1993).
Hoogenboom and Winter, "By-passing immunisation human antibodies from synthetic Erepertoires of germline V\\\subseript:H\\\ gene segments rearranged in Vitro" J. Mol. Biol. 227:381-388 ( 1992).
Hoogenboom et al., "Overview of antibody phage-display technology and its applications" Methods in Molecular Biology 178:1-37 (2002).
Hudson et al., "Engineered antibodies" Nature Medicine 9(1):129-134 (Jan. 2003).
Hughes-Jones et al., "Reaction between the isolated globular subunits of the complement component C1q and IgG-complexes" Molecular Immunology 16:697-701 ( 1979).
Idusogie et al. et al., "Engineered antibodies with increased activity to recruit complement" J Immunol 166(4):2571-2575 ( 2001).
Idusogie et al., "Mapping of the C1q Binding Site on Rituxan, A Chimeric Antibody with a Human IgG1 Fc" J Immunol 164(8):4178-4184 ( 2000).
Jeffrey et al., "Dipeptide-based highly potent doxorubicin antibody conjugates" Bioorganic & Medicinal Chemistry Letters 16:358-362 ( 2006).
Kabat et al. et al., Sequences Proteins Immunological Interest (NIH Publ. No. 91-3242), I:647-669 ( 1991).
Kam et al., "Carbon nanotubes as multifunctional biological transporters and near-infared agents for selective cancer cell destruction"P Natl Acad Sci USA 102(33):11600-11605 (Aug. 2005).
Kanda et al., "Comparison of cell lines for stable production of fucose-negative antibodies with enhanced ADCC" Biotechnol Bioeng 94(4):680-688 (Jul. 5, 2006).
Kim et al., "Localization of the site of the murine IgG1 molecule that is involved in binding to the murine intestinal Fc receptor" Eur J Immunol 24(10):2429-2434 (Oct. 1994).
Kindt et al. Kuby Immunology Sixth edition, New York:W. H. Freeman and Company,:91 (2007).
King et al., "Monoclonal antibody conjugates of doxorubicin prepared with branched peptide linkers: Inhibition of aggregation by methoxytriethyleneglycol chains" J Med Chem 45:4336-4343 ( 2002).
Klimka et al., "Human anti-CD30 recombinant antibodies by guided phage antibody selection using cell panning" BR J Cancer 83(2):252-260 ( 2000).
Kolb, William P., et al., "C1q: Isolation From Human Serum in High Yield Bysensitive Hemolytic Assayaffinity Chromatography and Development of a Highly" J Immunol 122(5):2103-2110 (May 1, 1979).

(56) References Cited

OTHER PUBLICATIONS

Kostelny et al., "Formation of a bispecific antibody by the use of leucine zippers" J Immunol 148(5):1547-1553 (Mar. 1, 1992).
Kozbor et al., "A Human Hybrid Myeloma for Production of Human Monoclonal Antibodies" U Immunol 133(6):3001-3005 (Dec. 1, 1984).
Kratz et al., "Prodrugs of anthracyclines in cancer chemotherapy" Curr Med Chem 13:477-523 ( 2006).
Lee et al., "Bivalent antibody phage display mimics natural immunoglobulin" J Immunol Methods 284(1-2):119-132 ( 2004).
Lee et al., "High-affinity human antibodies from phage-displayed synthetic Fab libraries with a single framework scaffold" J Mol Biol 340(5):1073-1093 (Jul. 23, 2004).
Li et al., "Human antibodies for immunotherapy development generated via a human B cell hybridoma technology" Proc Natl Acad Sci USA 103:3557-3562 ( 2006).
Li et al., "Optimization of humanized IgGs in glycoengineered Pichia pastoris" Nat Biotechnol 24(2):210-215 (Feb. 2006).
Lode et al., "Targeted therapy with a novel enediyene antibiotic calicheamicin V11 effectively suppresses growth and dissemination of liver metastases in a syngeneic model of murine neuroblastoma" Cancer Res 58:2925-2928 ( 1998).
Lonberg, "Fully human antibodies from transgenic mouse and phage display platforms" Current Opin Immunol 20:450-459 ( 2008).
Lonberg, "Human antibodies from transgenic animals" Nat Biotechnol 23(9):1117-1125 (Sep. 2005).
Lukas et al. et al., "Inhibition of C1-Mediated Immune Hemolysis by Monomeric and Dimeric Peptides from the Second Constant Domain of Human Immunoglobulin G\\\superscript:1\\\" J Immunol 127(6):2555-2560 (Dec. 1981).
Luo et al., "Structural Basis for the Dual Recognition of IL-12 and IL-23 by Ustekinumab" J. Mol. Biol. 402:797-812. (2010).
MacCallum et al. et al., "Antibody-antigen Interactions: Contact Analysis and Binding Site Topography" J Mol Biol 262:732-745 ( 1996).
Magistrelli et al., "Robust recombinant FcRn production in mammalian cells enabling oriented immobilization for IgG binding studies," Journal of Immunological Methods, vol. 375, Issues 1-2, Jan. 31, 2012, pp. 20-29.
Marks and Bradbury Methods Mol Biol, Antibody Engineering "Selection of :human antibodies from phage display libraries" Benny K. C. Lo,Humana Press, vol. 248:161-176 (2004).
Marks et al., "By-passing immunization, human antibodies from V-gene libraries displayed on phage" J Mol Biol 222:581-597 ( 1991).
Martin et al., "Peer Reviewed: Nanomaterials in Analytical Chemistry" Analytical Chemistry News & Features 70:322A-327A (May 1, 1998).
Mather et al., "Culture of testicular cells in hormone-supplemented serum-free medium" Ann NY Acad Sci 383:44-68 ( 1982).
Mather, "Establishment and characterization of two distinct mouse testicular epithelial cell lines" Biol Reprod 23:243-252 ( 1980).
McCafferty et al., "Phage Antibodies: Filamentous Phage Displaying Antibody Variable Domains" Nature 348:552-554 (Dec. 1990).
Milstein and Cuello et al., "Hybrid hybridomas and their use in immunohistochemistry" Nature 305:537-540 (Oct. 6, 1983).
Moreau, C., et al., "Structural and Functional Characterization of a Single-Chain Form of the Recognition Domain of Complement Protein C1q" Front Immunology 7 (Mar. 2, 2016).
Morgan et al., "The N-terminal end of the C\\\subscript:H\\\2 domain of chimeric human IgG1 anti-HLA-DR is necessary for C1q, Fcγ\\\RI and Fcγ\\\RIII binding" Immunology 86(2):319-324 (Oct. 1995).
Morrison et al., "Chimeric human antibody molecules: Mouse antigen-binding domains with human constant region domains" P Natl Acad Sci USA 81:6851-6855 (Nov. 1984).
Nagy, A. et al., "Stability of cytotoxic luteinizing hormone-releasing hormone conjugate (AN-152) containing doxorubicin 14-O-hemiglutarate in mouse and human serum in vitro: implications for the design of preclinical studies" Proc. Natl. Acad. Sci. USA 97(2):829-834 (2000).
Nethery, A., et al., "Single-step purification of immunoglobulin M on C1q-Sepharose" J Immunol Methods 126:57-60 (Jan. 1, 1990).
Ni, "Research progress and future perspectives in antibodomics and antibodomic drugs" Xiandai Mianyixue ((Abstract only)), 26(4):265-168 ( 2006).
Noren et al., "A general method for site-specific incorporation of unnatural amino acids into proteins" Science 244(4901):182-188 (Apr. 14, 1989).
Ochi et al. et al., "Functional immunoglobulin M production after transfection of cloned immunoglobulin heavy and light chain genes into lymphoid cells" P Natl Acad Sci USA 80:6351-6355 ( 1983).
Okazaki et al., "Fueose depletion from human IgG1 oligosaeeharide enhances binding enthalpy and association rate between IgG1 and FegammaRIIIa" J Mol Biol 336(5): 123 9-1249 (Mar. 5, 2004).
Osbourn et al., "From rodent reagents to human therapeutics using antibody guided selection" Methods 36:61-68 ( 2005).
Padlan, "A possible procedure for reducing the imrnunogenieity of antibody variable domains while preserving their ligand-binding properties" Mol Immunol 28(4/4):489-498 ( 1991).
Perkins et al., "Molecular modelling of human complement subcomponent C1q and its geomplex with C1r2C1s2 derived from neutron-scattering curves and hydrodynamic properties" Biochem. J. 228:13-26 ( 1985).
Petkova et al., "Enhanced half-life of genetically engineered human IgG1 antibodies in a humanized FeRn mouse model: potential application in humorally mediated autoimmune disease" International Immunology, 18:1759-1769 (2006).
Pfueller, Barbara, et al., "Successful treatment of patients with systemic lupus erythematosus by immunoadsorption with a C1q column: a pilot study." Arthritis Rheum 44(8):1962-1963 (Aug. 1, 2001).
Pluekthun et al. The Pharmacology of Monoclonal Antibodies Rosenburg and Moore (eds.), New York:Springer-Verlag, vol. 113:269-315 ( 1994).
Poon et al., "Conformation and Restricted Segmental Flexibility of C1, the First Component of Human Complement" J. Mol. Biol. 168:563-577 ( 1983).
Portolano et al., "Lack of promiscuity in autoantigen-specific H and L chain combinations as revealed by human H and L chain 'Roulette'" J Immunol 150(3):880-887 ( 1993).
Presta et al., "Humanization of an antibody directed against IgE" J Immunol 151(5):2623-2632 (Sep. 1, 1993).
Queen et al., "A humanized antibody that binds to the interleukin 2 receptor" P Natl Acad Sci USA 86(24):10029-10033 (Dec. 1989).
Radaev et al., "Recognition of IgG by Fcγ Receptor" J Biol Chem 276(19):16478-16483 (May 11, 2001).
Ravetch and Kinet, "Fc receptors" Annu Rev Immunol 9:457-492 ( 1991).
Reid et al., "Proteins involved in the activation and control of the two pathways of human complement" Biochem. Soc. Trans 11:1-12 ( 1983).
Riechmann et al., "Reshaping human antibodies for therapy" Nature 332(6162):323-327 (1988).
Ripka et al., "Two chinese hamster ovary glycosylation mutants affected in the conversion of GDP-mannose to GDP-fucose" Arch Biochem Biophys 249(2):533-545 (Sep. 1986).
Rosok et al., "A combinatorial library strategy for the rapid humanization of anticarcinoma BR96 Fab" J Biol Chem 271(37):22611-22618 (Sep. 13, 1996).
Roux et al., "Comparisons of the ability of human IgG3 hinge mutants, IgM, IgE, and IgA2, to form small immune complexes: a role for flexibility and geometry" J Immunol 161:4083-4090 ( 1998).
Sambrook et al. Molecular Cloning 2nd edition,Cold Spring Harbor Laboratory Press, ( 1989).
Sellar, Grant C., et al., "Characterization and organization of the genes encoding the A-, Band C-chains of human complement subcomponent C1q" J Biol Chem 274:481-490 (Aug. 21, 1990).
Shields et al. et al., "High resolution mapping of the binding site on human IgG1 for Fc gamma RI, Fc gamma RII, Fc gamma RIII, and

(56) References Cited

OTHER PUBLICATIONS

FcRn and design of IgG1 variants with improved binding to the Fc gamma. R" J Biol Chem 276(9):6591-6604 (Mar 2, 2001).

Shields et al. et al., "Lack of Fucose on Human IgG1 N-Linked Oligosaccharide Improves Binding to Human FcγRIII and Antibody-dependent Cellular Toxicity" J Biol Chem 277(30):26733-26740 (Jul. 26, 2002).

Sidhu et al., "Phage-displayed antibody libraries of synthetic heavy chain complementarity determining regions" J Mol Biol 338:299-310 ( 2004).

Simmons et al., "Expression of full-length immunoglobulins in *Escherichia coli*: rapid and efficient production of aglycosylated antibodies" J Immunol Methods 263:133-147 ( 2002).

Sims et al., "A Humanized CD18 Antibody Can Block Function Without Cell Destruction" J Immunol 151(4):2296-2308 (Aug. 15, 1993).

Singer, Oded, et al., "Silence of the genes" PNAS 101(15):5313-5314 (Apr. 13, 2004).

Sledge et al., "Binding Properties of the Human Complement Protein C1q" J. Biol. Chem. 248:2818-2823 ( 1973).

Svehag, S.E., et al., "Isolation of C1q-Binding Immune Complexes by Affinity Chromatography and Desorption with Diaminoalkyl Compound" Acta Path Microbiol. Scand. Sect. C 84:45-52 (Jan. 1, 1976).

Thielens, Nicole M., et al., "Further Characterization of the Interaction between the C1q Subcomponent of Human C1 and the Transmembrane Envelope Glycoprotein gp41 of HIV-1" J Immunol 151(11):6583-6592 (Dec. 1, 1993).

Thommesen et al., "Lysine 322 in the human IgG3 C(H)2 domain is crucial for antibody dependent complement activation" Mol Immunol 37(16):995-1004 (Nov. 2000).

Torgov et al., "Generation of an intensely potent anthracycline by a monoclonal antibody-(beta)-galactosidase conjugate" Bioconjugate Chemistry 16:717-721 ( 1991).

Traczewski and Rudnicka, "Briakinumab for the Treatment of Plaque Psoriasis" BioDrugs 26:9-20 (2012).

Traunecker et al., "Bispecific Single Chain Molecules (Janusins) Target Cytotoxic Lymphocytes on HIV Infected Cells" EMBO J 10(12):3655-3659 ( 1991).

Tutt et al., "Trispecific F(ab')\\\subscript:3\\\ derivatives that use cooperative signaling via the TCR/CD3 complex and CD2 to activate and redirect resting cytotoxic T cells" J Immunol 147(1):60-69 (Jul. 1991).

Umana et al., "Engineered glycoforms of an antineuroblastoma IgG1 with optimized gantibody-dependent cellular cytotoxic activity" Nat Biotechnol 17:176-180 (Feb. 1999).

Urlaub et al., "Isolation of Chinese hamster cell mutants deficient in dihydrofolate reductase activity" Proc Natl Acad Sci USA, 77(7):4216-4220 (Jul. 1980).

Uwatoko, Shu, et al., "Low-molecular weight C1q-binding immunoglobulin G in Patients with Systemic Lupus Erythematosus Consists of Aptoantibodies to the Collagen-like Region of C1q" J Clin Invest 82:816-824 (Sep. 12, 1988).

Van de Winkel et al., "Biology of Human Immunoglobulin G Fc Receptors" J Leukocyte Biol 49(5):511-524 (May 1991).

Van Dijk and van de Winkel, "Human antibodies as next generation therapeutics" Curr Opin Chem Biol 5(4):368-74 (Aug. 2001).

Vitetta et al., "Redesigning Nature's Poisons to Create Anti-Tumor Reagents" Science 1238(4830):1098-1104 (Nov. 20, 1987).

Vollmers and Brandlein, "Death by stress: natural IgM-induced apoptosis" Methods Find Exp Clin Pharmacol 27(3):185-191 ( 2005).

Vollmers and Brandlein, "The 'early birds': Natural IgM antibodies and immune surveillance" Histol Histopathol 20:927-937 ( 2005).

Weiss et al., "Functional Model of Subcomponent C1 of Human Complement" J.Mol. Biol. 189:573-581 ( 1986).

Winter et al., "Making antibodies by phage display technology" Annu Rev Immunol 12:433-455 ( 1994).

Wright et al., "Effect of glycosylation on antibody function: implications for genetic engineering" Trends Biotechnol. 15(1):26-32 ( 1997).

Yadav, Sunita, et al., "In Silico and In Vitro Studies on the Protein-Protein Interactions between Brugia malayi Immunomodulatory Protein Calreticulin and Human C1q" Plos One 9(9):e106413 (Sep. 3, 2014).

Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).

Yazaki, et al. Methods in Molecular Biology "Expression of recombinant antibodies in mammalian cell lines" Lo, B.K.C. (ed.), Totowa, NJ:Humana Press vol. 284:255-268 ( 2004).

Feng et al., Sichuan Science and Technology Press:376-379 (2013).

Gaboriaud et al., "The Crystal Structure of the Globular Head of Complement Protein C1q Provides a Basis for Its Versatile Recognition Properties" The Journal of Biological Chemistry 278:46974-46982 (2003).

Zhang Hefei University of Technology Press_2015_68 (English translation with CN version), pp. 68-78 (2015).

SEQUENCE LISTING

```
<160> NUMBER OF SEQ ID NOS: 23

<210> SEQ ID NO 1
<211> LENGTH: 223
<212> TYPE: PRT
<213> ORGANISM: Homo sapiens

<400> SEQUENCE: 1

Glu Asp Leu Cys Arg Ala Pro Asp Gly Lys Lys Gly Glu Ala Gly Arg
1               5                   10                  15
```

-continued

Pro Gly Arg Arg Gly Arg Pro Gly Leu Lys Gly Glu Gln Gly Glu Pro
            20                  25                  30

Gly Ala Pro Gly Ile Arg Thr Gly Ile Gln Gly Leu Lys Gly Asp Gln
        35                  40                  45

Gly Glu Pro Gly Pro Ser Gly Asn Pro Gly Lys Val Gly Tyr Pro Gly
    50                  55                  60

Pro Ser Gly Pro Leu Gly Ala Arg Gly Ile Pro Gly Ile Lys Gly Thr
65                  70                  75                  80

Lys Gly Ser Pro Gly Asn Ile Lys Asp Gln Pro Arg Pro Ala Phe Ser
                85                  90                  95

Ala Ile Arg Arg Asn Pro Pro Met Gly Gly Asn Val Val Ile Phe Asp
            100                 105                 110

Thr Val Ile Thr Asn Gln Glu Glu Pro Tyr Gln Asn His Ser Gly Arg
        115                 120                 125

Phe Val Cys Thr Val Pro Gly Tyr Tyr Tyr Phe Thr Phe Gln Val Leu
    130                 135                 140

Ser Gln Trp Glu Ile Cys Leu Ser Ile Val Ser Ser Arg Gly Gln
145                 150                 155                 160

Val Arg Arg Ser Leu Gly Phe Cys Asp Thr Thr Asn Lys Gly Leu Phe
                165                 170                 175

Gln Val Val Ser Gly Gly Met Val Leu Gln Leu Gln Gln Gly Asp Gln
            180                 185                 190

Val Trp Val Glu Lys Asp Pro Lys Lys Gly His Ile Tyr Gln Gly Ser
        195                 200                 205

Glu Ala Asp Ser Val Phe Ser Gly Phe Leu Ile Phe Pro Ser Ala
    210                 215                 220

<210> SEQ ID NO 2
<211> LENGTH: 22
<212> TYPE: PRT
<213> ORGANISM: Homo sapiens

<400> SEQUENCE: 2

Met Glu Gly Pro Arg Gly Trp Leu Val Leu Cys Val Leu Ala Ile Ser
1               5                   10                  15

Leu Ala Ser Met Val Thr
            20

<210> SEQ ID NO 3
<211> LENGTH: 226
<212> TYPE: PRT
<213> ORGANISM: Homo sapiens

<400> SEQUENCE: 3

Gln Leu Ser Cys Thr Gly Pro Pro Ala Ile Pro Gly Ile Pro Gly Ile
1               5                   10                  15

Pro Gly Thr Pro Gly Pro Asp Gly Gln Pro Gly Thr Pro Gly Ile Lys
            20                  25                  30

Gly Glu Lys Gly Leu Pro Gly Leu Ala Gly Asp His Gly Glu Phe Gly
        35                  40                  45

Glu Lys Gly Asp Pro Gly Ile Pro Gly Asn Pro Gly Lys Val Gly Pro
    50                  55                  60

Lys Gly Pro Met Gly Pro Lys Gly Gly Pro Gly Ala Pro Gly Ala Pro
65                  70                  75                  80

Gly Pro Lys Gly Glu Ser Gly Asp Tyr Lys Ala Thr Gln Lys Ile Ala
                85                  90                  95

```
Phe Ser Ala Thr Arg Thr Ile Asn Val Pro Leu Arg Arg Asp Gln Thr
                100                 105                 110
Ile Arg Phe Asp His Val Ile Thr Asn Met Asn Asn Asn Tyr Glu Pro
            115                 120                 125
Arg Ser Gly Lys Phe Thr Cys Lys Val Pro Gly Leu Tyr Tyr Phe Thr
        130                 135                 140
Tyr His Ala Ser Ser Arg Gly Asn Leu Cys Val Asn Leu Met Arg Gly
145                 150                 155                 160
Arg Glu Arg Ala Gln Lys Val Val Thr Phe Cys Asp Tyr Ala Tyr Asn
                165                 170                 175
Thr Phe Gln Val Thr Thr Gly Gly Met Val Leu Lys Leu Glu Gln Gly
            180                 185                 190
Glu Asn Val Phe Leu Gln Ala Thr Asp Lys Asn Ser Leu Leu Gly Met
        195                 200                 205
Glu Gly Ala Asn Ser Ile Phe Ser Gly Phe Leu Phe Pro Asp Met
    210                 215                 220
Glu Ala
225

<210> SEQ ID NO 4
<211> LENGTH: 27
<212> TYPE: PRT
<213> ORGANISM: Homo sapiens

<400> SEQUENCE: 4

Met Met Met Lys Ile Pro Trp Gly Ser Ile Pro Val Leu Met Leu Leu
1               5                   10                  15
Leu Leu Leu Gly Leu Ile Asp Ile Ser Gln Ala
            20                  25

<210> SEQ ID NO 5
<211> LENGTH: 217
<212> TYPE: PRT
<213> ORGANISM: Homo sapiens

<400> SEQUENCE: 5

Asn Thr Gly Cys Tyr Gly Ile Pro Gly Met Pro Gly Leu Pro Gly Ala
1               5                   10                  15
Pro Gly Lys Asp Gly Tyr Asp Gly Leu Pro Gly Pro Lys Gly Glu Pro
            20                  25                  30
Gly Ile Pro Ala Ile Pro Gly Ile Arg Gly Pro Lys Gly Gln Lys Gly
        35                  40                  45
Glu Pro Gly Leu Pro Gly His Pro Gly Lys Asn Gly Pro Met Gly Pro
    50                  55                  60
Pro Gly Met Pro Gly Val Pro Gly Pro Met Gly Ile Pro Gly Glu Pro
65                  70                  75                  80
Gly Glu Glu Gly Arg Tyr Lys Gln Lys Phe Gln Ser Val Phe Thr Val
                85                  90                  95
Thr Arg Gln Thr His Gln Pro Pro Ala Pro Asn Ser Leu Ile Arg Phe
            100                 105                 110
Asn Ala Val Leu Thr Asn Pro Gln Gly Asp Tyr Asp Thr Ser Thr Gly
        115                 120                 125
Lys Phe Thr Cys Lys Val Pro Gly Leu Tyr Tyr Phe Val Tyr His Ala
    130                 135                 140
Ser His Thr Ala Asn Leu Cys Val Leu Leu Tyr Arg Ser Gly Val Lys
145                 150                 155                 160
```

```
Val Val Thr Phe Cys Gly His Thr Ser Lys Thr Asn Gln Val Asn Ser
                165                 170                 175

Gly Gly Val Leu Leu Arg Leu Gln Val Gly Glu Glu Val Trp Leu Ala
            180                 185                 190

Val Asn Asp Tyr Tyr Asp Met Val Gly Ile Gln Gly Ser Asp Ser Val
            195                 200                 205

Phe Ser Gly Phe Leu Leu Phe Pro Asp
    210                 215

<210> SEQ ID NO 6
<211> LENGTH: 28
<212> TYPE: PRT
<213> ORGANISM: Homo sapiens

<400> SEQUENCE: 6

Met Asp Val Gly Pro Ser Ser Leu Pro His Leu Gly Leu Lys Leu Leu
1               5                   10                  15

Leu Leu Leu Leu Leu Pro Leu Arg Gly Gln Ala
            20                  25

<210> SEQ ID NO 7
<211> LENGTH: 134
<212> TYPE: PRT
<213> ORGANISM: Homo sapiens

<400> SEQUENCE: 7

Gln Pro Arg Pro Ala Phe Ser Ala Ile Arg Arg Asn Pro Pro Met Gly
1               5                   10                  15

Gly Asn Val Val Ile Phe Asp Thr Val Ile Thr Asn Gln Glu Glu Pro
            20                  25                  30

Tyr Gln Asn His Ser Gly Arg Phe Val Cys Thr Val Pro Gly Tyr Tyr
        35                  40                  45

Tyr Phe Thr Phe Gln Val Leu Ser Gln Trp Glu Ile Cys Leu Ser Ile
    50                  55                  60

Val Ser Ser Ser Arg Gly Gln Val Arg Arg Ser Leu Gly Phe Cys Asp
65                  70                  75                  80

Thr Thr Asn Lys Gly Leu Phe Gln Val Val Ser Gly Gly Met Val Leu
                85                  90                  95

Gln Leu Gln Gln Gly Asp Gln Val Trp Val Glu Lys Asp Pro Lys Lys
            100                 105                 110

Gly His Ile Tyr Gln Gly Ser Glu Ala Asp Ser Val Phe Ser Gly Phe
        115                 120                 125

Leu Ile Phe Pro Ser Ala
    130

<210> SEQ ID NO 8
<211> LENGTH: 132
<212> TYPE: PRT
<213> ORGANISM: Homo sapiens

<400> SEQUENCE: 8

Thr Gln Lys Ile Ala Phe Ser Ala Thr Arg Thr Ile Asn Val Pro Leu
1               5                   10                  15

Arg Arg Asp Gln Thr Ile Arg Phe Asp His Val Ile Thr Asn Met Asn
            20                  25                  30

Asn Asn Tyr Glu Pro Arg Ser Gly Lys Phe Thr Cys Lys Val Pro Gly
        35                  40                  45
```

-continued

```
Leu Tyr Tyr Phe Thr Tyr His Ala Ser Ser Arg Gly Asn Leu Cys Val
         50                  55                  60

Asn Leu Met Arg Gly Arg Glu Arg Ala Gln Lys Val Val Thr Phe Cys
 65                  70                  75                  80

Asp Tyr Ala Tyr Asn Thr Phe Gln Val Thr Thr Gly Gly Met Val Leu
                 85                  90                  95

Lys Leu Glu Gln Gly Glu Asn Val Phe Leu Gln Ala Thr Asp Lys Asn
                100                 105                 110

Ser Leu Leu Gly Met Glu Gly Ala Asn Ser Ile Phe Ser Gly Phe Leu
            115                 120                 125

Leu Phe Pro Asp
        130
```

<210> SEQ ID NO 9
<211> LENGTH: 129
<212> TYPE: PRT
<213> ORGANISM: Homo sapiens

<400> SEQUENCE: 9

```
Lys Phe Gln Ser Val Phe Thr Val Thr Arg Gln Thr His Gln Pro Pro
 1               5                  10                  15

Ala Pro Asn Ser Leu Ile Arg Phe Asn Ala Val Leu Thr Asn Pro Gln
                20                  25                  30

Gly Asp Tyr Asp Thr Ser Thr Gly Lys Phe Thr Cys Lys Val Pro Gly
            35                  40                  45

Leu Tyr Tyr Phe Val Tyr His Ala Ser His Thr Ala Asn Leu Cys Val
         50                  55                  60

Leu Leu Tyr Arg Ser Gly Val Lys Val Val Thr Phe Cys Gly His Thr
 65                  70                  75                  80

Ser Lys Thr Asn Gln Val Asn Ser Gly Gly Val Leu Leu Arg Leu Gln
                 85                  90                  95

Val Gly Glu Glu Val Trp Leu Ala Val Asn Asp Tyr Tyr Asp Met Val
                100                 105                 110

Gly Ile Gln Gly Ser Asp Ser Val Phe Ser Gly Phe Leu Leu Phe Pro
            115                 120                 125

Asp
```

<210> SEQ ID NO 10
<211> LENGTH: 4
<212> TYPE: PRT
<213> ORGANISM: Artificial Sequence
<220> FEATURE:
<223> OTHER INFORMATION: peptidic linker

<400> SEQUENCE: 10

```
Arg Tyr Lys Gln
 1
```

<210> SEQ ID NO 11
<211> LENGTH: 5
<212> TYPE: PRT
<213> ORGANISM: Artificial Sequence
<220> FEATURE:
<223> OTHER INFORMATION: peptidic linker

<400> SEQUENCE: 11

```
Gly Asp Tyr Lys Ala
 1               5
```

```
<210> SEQ ID NO 12
<211> LENGTH: 9
<212> TYPE: PRT
<213> ORGANISM: Artificial Sequence
<220> FEATURE:
<223> OTHER INFORMATION: peptidic linker

<400> SEQUENCE: 12

Gly Gly Gly Ser Gly Asp Tyr Lys Ala
1               5

<210> SEQ ID NO 13
<211> LENGTH: 5
<212> TYPE: PRT
<213> ORGANISM: Artificial Sequence
<220> FEATURE:
<223> OTHER INFORMATION: peptidic linker

<400> SEQUENCE: 13

Met Glu Ala Lys Asp
1               5

<210> SEQ ID NO 14
<211> LENGTH: 9
<212> TYPE: PRT
<213> ORGANISM: Artificial Sequence
<220> FEATURE:
<223> OTHER INFORMATION: peptidic linker

<400> SEQUENCE: 14

Met Glu Ala Gly Gly Asn Ile Lys Asp
1               5

<210> SEQ ID NO 15
<211> LENGTH: 21
<212> TYPE: PRT
<213> ORGANISM: Artificial Sequence
<220> FEATURE:
<223> OTHER INFORMATION: HIS-AVITAG

<400> SEQUENCE: 15

His His His His His His Gly Leu Asn Asp Ile Phe Glu Ala Gln Lys
1               5                   10                  15

Ile Glu Trp His Glu
            20

<210> SEQ ID NO 16
<211> LENGTH: 107
<212> TYPE: PRT
<213> ORGANISM: Homo sapiens

<400> SEQUENCE: 16

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95
```

Ala Pro Ile Glu Lys Thr Ile Ser Lys Ala Lys
              100                 105

<210> SEQ ID NO 17
<211> LENGTH: 106
<212> TYPE: PRT
<213> ORGANISM: Homo sapiens

<400> SEQUENCE: 17

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 18
<211> LENGTH: 330
<212> TYPE: PRT
<213> ORGANISM: Homo sapiens

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 19
<211> LENGTH: 326
<212> TYPE: PRT
<213> ORGANISM: Homo sapiens

<400> SEQUENCE: 19

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
```

```
            245                 250                 255
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 20
<211> LENGTH: 377
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

```
Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 21
<211> LENGTH: 330
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Arg Leu Thr Val Asp Lys Ser Arg Trp Gln Glu Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
            325                 330

<210> SEQ ID NO 22
<211> LENGTH: 227
<212> TYPE: PRT
<213> ORGANISM: Artificial Sequence
<220> FEATURE:
<223> OTHER INFORMATION: Fc-Region

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 23
<211> LENGTH: 5
<212> TYPE: PRT
<213> ORGANISM: Artificial Sequence
<220> FEATURE:
<223> OTHER INFORMATION: linker X3

<400> SEQUENCE: 23

Gly Gly Gly Gly Ser
1               5
```

COMPLEMENT FACTOR BASED AFFINITY CHROMATOGRAPHY

CROSS REFERENCE TO RELATED APPLICATIONS

This application is a continuation of International Application No. PCT/EP2017/073402 having an International Filing Date of Sep. 18, 2017, which claims the benefit of priority to European Patent Application No. 16189372.2 filed on Sep. 19, 2016, the entire contents of which are incorporated herein by reference.

SEQUENCE LISTING

The instant application contains a Sequence Listing submitted electronically in ASCII format and is hereby incorporated herein by reference in its entirety. Said ASCII copy, created Mar. 8, 2019, is named P33852-US_Sequence_Listing.txt and is 27,789 bytes in size.

Herein is reported the use of an affinity chromatography column comprising immobilized human C1q as affinity ligand and its use.

BACKGROUND

An immunoglobulin in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

The inborn immunity of humans comprises the complement pathway. This pathway is activated by the binding of C1q, the recognition subunit of the C1 complement factor, to an immunological target. The full C1q molecule is a heteromeric molecule comprising six copies of each of the three monomeric building blocks, which are denoted as C1qA, C1qB, and C1qC. Each of the monomeric units comprises an N-terminal region (of 3 to 9 residues), a collagen-like domain (spanning approximately 81 residues), and a globular domain (globular head; spanning approximately 135 residues) (Sellar, G. C., et al. Biochem. J. 274 (1991) 481-490). C1q has the function of a recognition unit and can bind to the CH2 domain of IgG1 as well as the CH3 or CH4 domains of IgM (Ghebrehiwet, B., et al., J. Exp. Med. 160 (1984) 1375-1389).

In WO 2010/048313 recombinant FcRn and variants thereof for purification of Fc-containing fusion proteins is reported. Magistrelli, G., et al. report robust recombinant FcRn production in mammalian cells enabling oriented immobilization for IgG binding studies (J. Immunol. Meth. 371 (2012) 20-29). In WO 2013/120929 is reported the use of an immobilized non-covalent complex of a neonatal Fc receptor (FcRn) and beta-2-microglobulin (b2m) as affinity chromatography ligand in general and, for example, for the determination of the in vivo half-live of an antibody by determining the ratio of the retention times of the antibody and a reference antibody. Human C1q has been purified using an affinity chromatography with immobilized human IgG (see e.g. Assimeh, S. N., et al., J. Immunol. 113 (1974) 225-234; Kolb, W. P., et al., J. Immunol. 122 (1979) 2103-2111)

Bally, I., et al. reported the production of full-length human C1q involving stable transfection of HEK 293-F mammalian cells and fusion of an affinity tag to the C-terminal end of the C chain (Proc. Natl. Acad. Sci. USA 110 (2013) 8650-8655). The resulting recombinant (r) C1q molecule is reported to be similar to serum C1q as judged from biochemical and structural analyses and shall exhibit the characteristic shape of a bunch of flowers. Analysis of its interaction properties by surface plasmon resonance showed that rC1q retains the ability of serum C1q to associate with the C1s-C1r-C1r-C1s tetramer, to recognize physiological C1q ligands such as IgG. The affinity tag was used for purifying the recombinant C1 q.

Svehag, S.-E. and B, D. reported the isolation of C1q-binding immune complexes by affinity chromatography and desorption with a diaminoalkyl compound (Acta Path. Microbiol. Scand. Sect. C 84 (1976) 45-52). Temperature-sensitive binding of solid phase C1q to aggregated human immunoglobulin G was reported by Gibbons, J. J. Jr., et al. (Biochim. Biophys. Acta 670 (1981) 146-149). The isolation of monomeric C1q-binding IgG from five SLE plasmas by C1q affinity chromatography and gel filtration was reported by Uwatoko, S. and Mannik, M. (J. Clin. Invest. 82 (1982) 816-824). The coupling of C1q to agarose and the use of such material for the purification of C1qR was reported by Ghebrehiwet, B., et al. (J. Exp. Med. 160 (1984) 1375-1389). Nethery, A., et al. (J. Immunol. Meth. 126 (1990) 57-60) reported the single-step purification of immunoglobulin M on C1q-Sepharose. The isolation of monomeric C1q-binding IgG from five SLE plasmas by C1q affinity chromatography and gel filtration was reported by Uwatoko, S. and Mannik, M. (J. Clin. Invest. 82 (1982) 816-824).

Moreau, C., et al. (Front. Immunol. 7 (2016) Article 79) reported the production of a single-chain recombinant form of human C1q globular region (C1q-scGR) comprising in N- to C-terminal direction residues 88-223 of C1qA, a Gly-Ser-Gly linker, residues 87 to 217 of C1qC, a Gly-Ser-Ala linker, and residues 90 to 226 of C1qB (page 2 and FIG. 1). The 5'-3' A-C-B order chosen to generate C1q-scGR also corresponds to that of the three C1q genes on chromosome 1p.

Pfueller, B., et al. (Arth. Rheum. 44 (2001) 1962-1963) disclosed the results of a pilot study in the successful treatment of patients with systemic lupus erythematosus by immunoadsorption with a C1q column using C1q isolated from porcine plasma.

US 2015/329606 disclosed a method a method for recombinant production of a C1q protein or a variant of the C1q protein, in which the protein is recovered from an in vitro culture of cells expressing a C1qA subunit or a variant of the C1qA subunit, a C1qB subunit or a variant of the C1qB subunit, and a C1qC subunit or a variant of the C1qC subunit, in which at least one of the subunits or subunit variants also has at the N-terminus or C-terminus a sequence of amino acids of at least six residues, at least 40% of which are glutamic acid and/or aspartic acid residues.

Moreau, C., et al. disclosed the structural and functional characterization of a single-chain form of the recognition domain of complement protein C1q (Front. Immunol. 7 (2016).

Yadav, S., et al. disclosed in silico and in vitro studies on the protein-protein interactions between brugia malayi immunomodulatory protein calreticulin and human C1q (PLOS ONE 9 (2014) e106413).

US 2005/208586 disclosed polypeptides or non-polypeptides derived from C1q, a subunit of the first complement component molecule C1.

SUMMARY

One aspect as reported herein is the use of a fusion polypeptide comprising fragments of the Complement C1q subcomponent subunit A to C as affinity chromatography ligand.

It has been found that with the fusion polypeptide as reported herein it is now possible to separate, isolate and characterize with respect to their in vivo properties closely related antibody species, i.e. differing in a single or a limited number of amino acid residues, or differing in the glycosylation pattern, which influences the interaction between the analyte and the fusion polypeptide, i.e. the interaction of an Fc-region with C1q.

Thus, with the method as reported herein it is possible to separate different variants of one parent antibody and to determine the specific ratio between these variants, which is not possible with the currently known methods as these only provide the sum of the modifications and not the individual species (i.e. for a mixture of parent and variant 1 and variant 2 and variant 1/2 the mass spectrometry provides for the total of variant 1 comprising molecules, i.e. variants comprising a single variation (1) and also those comprising also the second variation (1/2)).

It has been found that for the given conditions a wild-type IgG1 antibody has a retention time of about 25 to 28 minutes under the conditions as outlined in the Examples provided herein.

An antibody having a modified Fc-region with reduced C1q binding has a retention time that is smaller, whereas an antibody having a modified Fc-region with enhanced C1q binding has a retention time that is bigger compared to an antibody having the parental unmodified Fc-region.

One aspect as reported herein is a fusion polypeptide according to formula I

TAG-X1-C1qA-X2-C1qB-X3-C1qC-X4    (formula I)

wherein
X1 denotes a first peptidic linker,
X2 denotes a second peptidic linker,
X3 denotes a third peptidic linker,
X4 denotes a fourth peptidic linker,
X1, X2, X3, X4 are independently of each other either present or absent,
TAG is an amino acid sequence tag,
TAG can be present or absent,
C1qA is a fragment of SEQ ID NO: 01,
C1qB is a fragment of SEQ ID NO: 03,
C1qC is a fragment of SEQ ID NO: 05, and
- denotes a peptide bond.

In one embodiment X1, X2 and X3 are present and X4 is absent.

In one embodiment X2, X3 and X4 are present and X1 is absent.

In one embodiment X1 has the amino acid sequence of SEQ ID NO: 10, X2 has the amino acid sequence of SEQ ID NO: 11 or 12, X3 has the amino acid sequence of SEQ ID NO: 13 or 14, and X4 is absent.

In one embodiment X1 is absent, X2 has the amino acid sequence of SEQ ID NO: 13 or 14, X3 has the amino acid sequence of SEQ ID NO: 11 or 12, and X4 has the amino acid sequence of SEQ ID NO: 10.

In one embodiment C1qA has the amino acid sequence of SEQ ID NO: 07, C1qB has the amino acid sequence of SEQ ID NO: 08, and C1qC has the amino acid sequence of SEQ ID NO: 09.

In one embodiment TAG is present and has the amino acid sequence of SEQ ID NO: 15.

In one embodiment X3 is present and has the amino acid sequence GGGGS (SEQ ID NO: 23).

In one embodiment formula I denotes from right to left in N- to C-terminal direction the sequence of the elements of the fusion polypeptide (N-term.-C1 qC-C1 qB-C1 qA-C-term.).

One aspect as reported herein is a multimeric non-covalent complex comprising 2 to 6 fusion polypeptides as reported herein.

In one embodiment in at least one of the fusion polypeptides of the non-covalent complex TAG is present and in at least one of the fusion polypeptides of the non-covalent complex TAG is absent.

One aspect as reported herein is the use of a fusion polypeptide as reported herein or of a multimeric complex as reported herein as affinity chromatography ligand in an affinity chromatography.

In one embodiment the fusion polypeptide or the complex is immobilized on a solid phase. In one embodiment the fusion polypeptide or the multimeric complex is biotinylated and the solid phase is derivatized with streptavidin.

In one embodiment the affinity chromatography is for separating antibodies or fusion polypeptides comprising at least an Fc-region. In one embodiment the affinity chromatography is an analytical affinity chromatography. In one embodiment the affinity chromatography is with collection of fractions or without collection of fractions.

In one embodiment the solid phase is a chromatography material. In one embodiment the chromatography material is sepharose (crosslinked agarose).

In one embodiment the use is for the determination of the in vivo half-live of an antibody by determining the ratio of the retention times of the antibody and a reference antibody.

In one embodiment the use is for screening a library of modified antibodies or modified fusion polypeptides of a parent antibody or a parent fusion polypeptide which comprise at least an C1q binding portion of an Fc-region for those modified antibodies or modified fusion polypeptides that have an altered binding affinity for C1q compared to the parent antibody or parent fusion polypeptide.

In one embodiment the use is for identifying antibodies or fusion polypeptides that comprise at least a C1q-binding portion of an Fc-region which exhibit altered binding to C1q.

In one embodiment the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

In one embodiment the use is in an affinity chromatography with a salt gradient.

In one embodiment the use is for the determination of the in vivo half-live of an antibody by determining the ratio of the retention times of the antibody and a reference antibody.

In one embodiment the use is for the separating of antibodies or fusion polypeptides comprising at least an Fc-region.

In one embodiment the use is for determining the glycosylation of an antibody.

In one embodiment the use is for identifying antibodies or fusion polypeptides that comprise at least a C1q-binding portion of an Fc-region which exhibit altered binding to C1q.

One aspect as reported herein is a method for selecting an antibody with a predetermined in vivo half-live wherein a chromatography is performed and an antibody is selected that has a retention time within a given retention time window relative to a wild-type IgG1.

DETAILED DESCRIPTION OF EMBODIMENTS OF THE INVENTION

Figure 1:
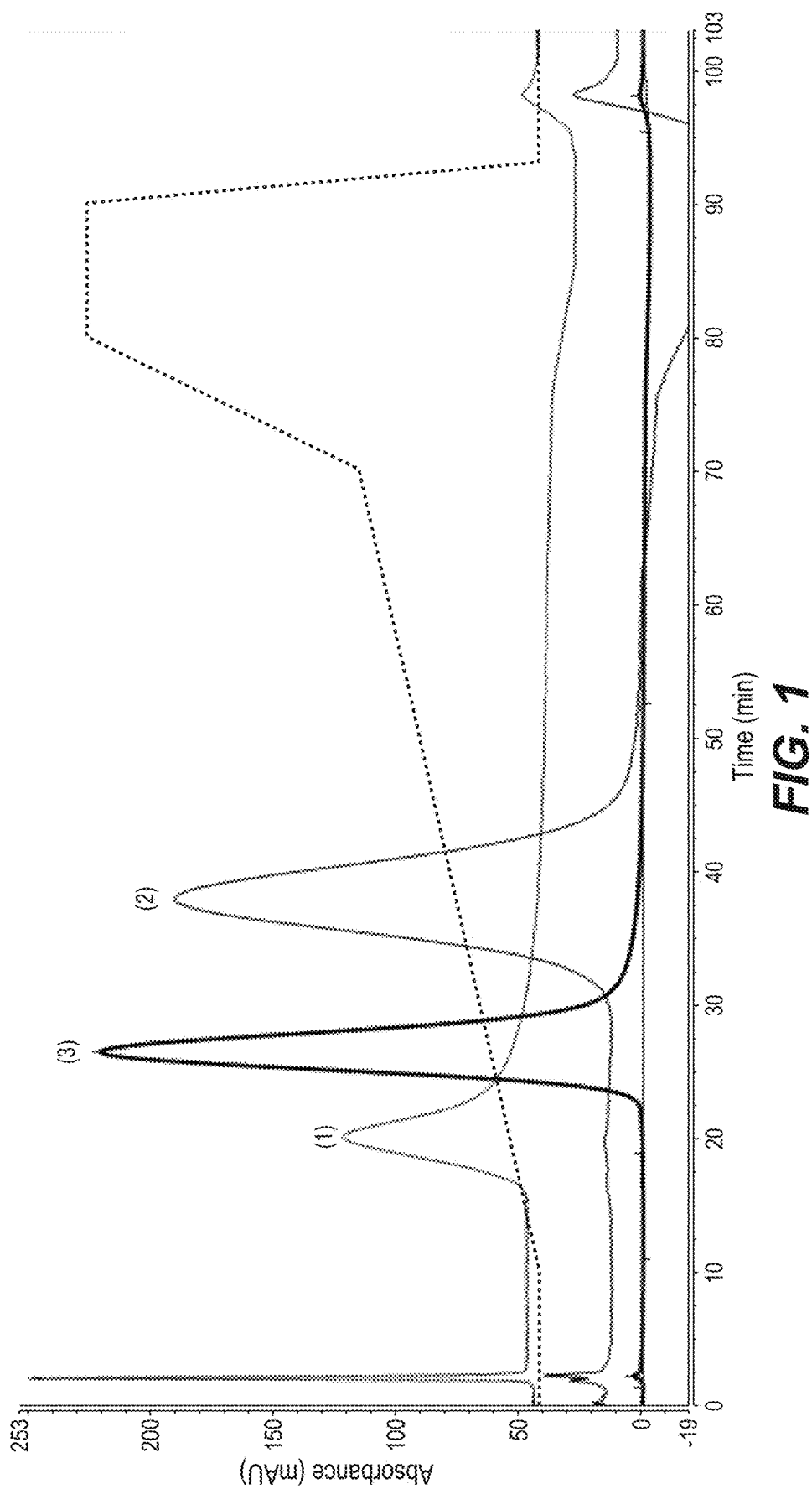
FIG. 1 Overlay of exemplary chromatograms of an antibody of the IgG1 subclass (3) and an antibody of the IgG3 subclass (2) and an antibody of the IgG4 subclass (1). The dotted line represents the course of the ionic strength gradient.

The invention is at least in part based on the finding that a single chain recombinant C1q comprising the Complement C1q subcomponent subunits in the sequence A-B-C has improved properties. For example it can be used as affinity chromatography ligand for the analysis and separation of antibodies and Fc-region comprising polypeptides.

As known to a person skilled in the art enables the use of recombinant DNA technology the production of numerous derivatives of a nucleic acid and/or polypeptide. Such derivatives can, for example, be modified in one individual or several positions by substitution, alteration, exchange, deletion, or insertion. The modification or derivatization can, for example, be carried out by means of site directed mutagenesis. Such modifications can easily be carried out by a person skilled in the art (see e.g. Sambrook, J., et al., Molecular Cloning: A Laboratory Manual, Cold Spring Harbor Laboratory Press, New York, USA (1989); Hames, B. D. and Higgins, S. J., Nucleic acid hybridization—a practical approach, IRL Press, Oxford, England (1985)). The use of recombinant technology enables a person skilled in the art to transform various host cells with heterologous nucleic acid(s). Although the transcription and translation, i.e. expression, machinery of different cells use the same elements, cells belonging to different species may have among other things a different so-called codon usage. Thereby identical polypeptides (with respect to amino acid sequence) may be encoded by different nucleic acid(s). Also, due to the degeneracy of the genetic code, different nucleic acids may encode the same polypeptide.

The use of recombinant technology enables the transformation of various host cells with heterologous nucleic acid(s). Although the transcription and translation, i.e. expression, machinery of different cells use the same elements, cells belonging to different species may have among other things a different so-called codon usage.

Thereby identical polypeptides (with respect to amino acid sequence) may be encoded by different nucleic acid(s). Also, due to the degeneracy of the genetic code, different nucleic acids may encode the same polypeptide.

Within the scope of the present invention, transfected cells may be obtained with substantially any kind of transfection method known in the art. For example, the nucleic acid may be introduced into the cells by means of electroporation or microinjection. Alternatively, lipofection reagents such as FuGENE 6 (Roche Diagnostics GmbH, Germany), X-tremeGENE (Roche Diagnostics GmbH, Germany), and LipofectAmine (Invitrogen Corp., USA) may be used. Still alternatively, the nucleic acid may be introduced into the cell by appropriate viral vector systems based on retroviruses, lentiviruses, adenoviruses, or adeno-associated viruses (Singer, O., Proc. Natl. Acad. Sci. USA 101 (2004) 5313-5314).

I. Definitions

Methods and techniques useful for carrying out the current invention are known to a person skilled in the art and are described e.g. in Thielens, N. M., et al., J. Immunol. 151 (1993) 6583-6592; Ausubel, F. M., ed., Current Protocols in Molecular Biology, Volumes I to III (1997), and Sambrook et al., Molecular Cloning: A Laboratory Manual, Second Edition, Cold Spring Harbor Laboratory Press, Cold Spring Harbor, N.Y. (1989). As known to a person skilled in the art enables the use of recombinant DNA technology the production of numerous derivatives of a nucleic acid and/or polypeptide. Such derivatives can, for example, be modified in one individual or several positions by substitution, alteration, exchange, deletion, or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1989) Cold Spring Harbor Laboratory Press, New York, USA). The use of recombinant technology enables a person skilled in the art to transform various host cells with one or more heterologous nucleic acids. Although the transcription and translation, i.e. expression, machinery of different cells use the same elements, cells belonging to different species may have among other things a different so-called codon usage. Thereby identical polypeptides (with respect to amino acid sequence) may be encoded by different nucleic acid(s). Also, due to the degeneracy of the genetic code, different nucleic acids may encode the same polypeptide.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein.

The term "alteration" denotes the substitution, addition, or deletion of one or more amino acid residues in a parent antibody or fusion polypeptide comprising at least an FcRn binding portion of an Fc-region to obtain a modified antibody or fusion polypeptide.

The term "amino acid substitution" denotes the replacement of at least one existing amino acid residue with another different amino acid residue (replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "amino acid insertion" denotes the incorporation of at least one amino acid residue at a predetermined position in an amino acid sequence. In one embodiment the insertion will be the insertion of one or two amino acid residues. The inserted amino acid residue(s) can be any naturally occurring or non-naturally occurring amino acid residue.

The term "amino acid deletion" denotes the removal of at least one amino acid residue at a predetermined position in an amino acid sequence.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit FcRn-binding property.

The term "buffer substance" denotes a substance that when in solution can level changes of the pH value of the solution e.g. due to the addition or release of acidic or basic substances.

C1q (Complement C1q subcomponent) is assembled from three polypeptide chains (A, B and C) encoded by 3 different genes (C1QA, C1QB and C1QC). Each chain comprises an N-terminal collagen-like sequence and a C-terminal globular gC1q module, with disulfide bridges linking the N-terminal ends of the A and B chains and two C chains. Each A-B dimer associates with a C chain, resulting in a basic subunit comprised of two disulphide-linked heterotrimeric collagen-like stalks prolonged by globular domains. The association of 3 subunits results in a full-length protein with a typical shape of a bouquet of six flowers, the stalks being held together in their N-terminal half through strong non-covalent interactions and then diverging to form six individual stems, each terminating in a globular head (see Frachet, P., et al. in "Autoimmunity—Pathogenesis, Clinical Aspects and Therapy of Specific Autoimmune Diseases", ed. by K. Chatzidionysiou, INTECH open source publishing, 2015, DOI: 10.5772/60519).

The term "C1q binding" denotes the binding of C1q to an antibody bound to its antigen. The binding of the antibody to its antigen is without limitation in vivo and in vitro within the methods and assays as reported herein.

In one embodiment C1q binding is determined in a method comprising i) coating a multi-well plate (e.g. a 96-well ELISA plate) overnight at 4° C. with antibody in PBS at a concentration ranging from 0.007 to 25.0 mg/mL, ii) washing the plates, iii) blocking remaining reactive surface residues with 0.5×PBS/0.025% Tween 20/0.1% gelatin, iv) incubating the multi-well plates for one hour at 37° C. with a) 3% pooled human serum, b) rabbit anti-human C1q, and c) swine anti-rabbit IgG antibody conjugated to HRP, comprising in-between washing, v) incubating for about 30 min with 1 mg/mL 2,2'-azino-bis 3-ethylbenzothiazoline-6-sulfonic acid, vi) adding 100 µL 2% oxalic acid, and vii) measuring the absorbance at 405 nm in a microplate reader.

C1q binding of an antibody denotes herein a multivalent interaction resulting in high avidity binding.

The term "CH2 domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 16: APELLGG PSVFLFPPKP KDTLMISRTP EVTCVWDVS HEDPE-VKFNW YVDGVEVHNA KTKPREEQ E STYRWSVLT VLHQDWLNGK EYKCKVSNKA LPAPIEKTIS KAK.

The term "CH3 domain" denotes the part of an antibody heavy chain polypeptide that extends approximately from EU position 341 to EU position 446. In one embodiment the CH3 domain has the amino acid sequence of SEQ ID NO: 17: GQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG.

The term "class" of an antibody denotes the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "comprising" when used herein expressly includes the term "consisting of".

The term "complement activation" denotes the initiation of the classical complement pathway. This initiation results from the binding of complement component C1q to the antibody-antigen complex. C1q is the first protein in the classical complement cascade. It is involved in a series of reactions that result in the formation of an active C3 convertase, which cleaves complement component C3 into C3b and C3a. C3b binds to membrane C5 resulting in so called C5b which triggers the late events of complement activation (assembly of C5b, C6, C7, C8 and C9 into the membrane attack complex (MAC)). Finally the complement cascade results in the formation of pores in the cell wall causing cell lysis (aka complement dependent cytotoxicity, CDC).

The term "complement-dependent cytotoxicity (CDC)" refers to lysis of cells induced by the antibody as reported herein in the presence of complement. CDC is measured in one embodiment by the treatment of CD19 expressing human endothelial cells with an antibody as reported herein in the presence of complement. The cells are in one embodiment labeled with calcein. CDC is found if the antibody induces lysis of 20% or more of the target cells at a concentration of 30 µg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzothiazoline-6-sulfonate (6)]).

The term "derived from" denotes that the respective amino acid sequence comprises the same amino acid sequence, or contains amino acid sequence changes, or is a shortened variant or a fused variant of a parent amino acid sequence.

"Effector functions" refer to those biological activities attributable to the Fc region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 22. However, the C-terminal lysine (Lys447) of the Fc-region may or may not be present.

The antibodies as used in the methods as reported herein comprise an Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A (numbering according to EU index of Kabat).

The term "full length antibody" denotes an antibody having a structure substantially similar to a native antibody structure or having heavy chains that contain an Fc-region as defined herein.

The term "hinge region" denotes the part of an antibody heavy chain polypeptide that joins the CH1 domain and the CH2 domain, e. g. from about position 216 to position about 230 according to the EU number system of Kabat. The hinge region is normally a dimeric molecule consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (Roux, et al., J. Immunol. 161 (1998) 4083).

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g. the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice, hamster and rats). In certain embodiments, the individual or subject is a human.

The term "monoclonal antibody" denotes an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be constructed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa ($\kappa$) and lambda ($\lambda$), based on the amino acid sequence of its constant domain.

The term "non-naturally occurring amino acid residue" denotes an amino acid residue, other than the naturally occurring amino acid residues as listed above, which can be covalently bound to the adjacent amino acid residues in a polypeptide chain. Examples of non-naturally occurring amino acid residues are norleucine, omithine, norvaline, homoserine. Further examples are listed in Ellman, et al., Meth. Enzym. 202 (1991) 301-336. Exemplary method for the synthesis of non-naturally occurring amino acid residues are reported in, e. g., Noren, et al., Science 244 (1989) 182 and Ellman et al., supra.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The terms "variant", "modified antibody", and "modified fusion polypeptide" denotes molecules which have an amino acid sequence that differs from the amino acid sequence of a parent molecule. Typically such molecules have one or more alterations, insertions, or deletions. In one embodiment the modified antibody or the modified fusion polypeptide comprises an amino acid sequence comprising at least a portion of an Fc-region which is not naturally occurring. Such molecules have less than 100% sequence identity with the parent antibody or parent fusion polypeptide. In one embodiment the variant antibody or the variant fusion polypeptide has an amino acid sequence that has from about 75% to less than 100% amino acid sequence identity with the amino acid sequence of the parent antibody or parent fusion polypeptide, especially from about 80% to less than 100%, especially from about 85% to less than 100%, especially from about 90% to less than 100%, and especially from about 95% to less than 100%. In one embodiment the parent antibody or the parent fusion polypeptide and the variant antibody or the variant fusion polypeptide differ by one (a single), two or three amino acid residue(s).

II. Compositions and Methods

Typically, a non-human antibody that is intended to be used as therapeutic is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of or a full length human constant region. In some embodiments, some FR residues in a humanized antibody are substituted with corresponding residues from a non-human antibody (e.g. the antibody from which the HVR residues are derived), e.g. to restore or improve antibody specificity or affinity.

Antibodies contain two binding sites for certain Fc receptors, such as Fcgamma receptor or FcRn, as well as for the complement system, i.e. for C1q. One binding site is in each heavy chain Fc-region. The binding of the Fc-region to C1q mediates complement dependent cytotoxicity (CDC), wherein C1q forms a complex with the serine proteases C1r and C1s to form the C1 complex.

The three dimensional structure of C1q is like a bunch of tulips comprising six globular heads, which comprise the antibody binding regions (see e.g. Perkins et al., Biochem. J. 228 (1985) 13-26; Poon et al., J. Mol. Biol. 168 (1983) 563-577; Reid et al., Biochem. Soc. Trans. 11 (1983) 1-12; Weiss et al., J. Mol. Biol. 189 (1986) 573-581). In more detail, C1q comprises 18 subunits, each 6 A subunits, 6 B subunits and 6 C subunits. Each trimer of A-, B- and C-subunit forms an Fc-region binding site. Thus, fully assembled C1q is capable of binding six Fc-regions.

The different IgG subclasses have different affinity for C1q, for example IgG1 and IgG3 shows strong C1q binding, whereas IgG2 and IgG4 poorly bind to complement. Thereby IgG1 and IgG3 exhibit strong CDC, IgG2 shows weak CDC and IgG4 shows no CDC.

In the binding of the Fc-region to C1q residues in the hinge region as well as the CH2 domain are involved. These regions have different amino acid sequences in IgG1/IgG3 compared to IgG2/IgG4. For example exchange of residues 233-236 (numbering according the EU index of Kabat) influenced CDC greatly (see e.g. Armour, K. L., Eur. J. Immunol. 29 (1999) 2613-2624; and Shields et al., J. Biol. Chem. 276 (2001) 6591-6604). Further mutagenesis studies have identified that the C1q binding site on human IgG encompasses amino acid residues D270, K322, K326, P329, and P331, and E333 (Idusogie et al., J. Immunol. 164 (2000) 4178-4184; Idusogie et al., J. Immunol. 166 (2001) 2571-2575).

The antibody Fc-region further has a conserved N-linked glycosylation site at amino acid residue N297. This glycosylation is required for efficient C1q-Fc-region interaction. Modifications in the composition of the N297 carbohydrate or its elimination affects binding (see e.g. Umana et al., Nat. Biotechnol. 17 (1999) 176-180; Davies et al., Biotechnol. Bioeng. 74 (2001) 288-294; Mimura et al., J. Biol. Chem.

276 (2001) 45539-45547; Radaev et al., J. Biol. Chem. 276 (2001) 16478-16483; Shields et al., J. Biol. Chem. 276 (2001) 6591-6604; Shields et al., J. Biol. Chem. 277 (2002) 26733-26740; Simmons et al., J. Immunol. Meth. 263 (2002) 133-147).

For complement activation more than a single antibody Fc-region is required as the affinity of monomeric IgG for C1q is quite weak (affinity about $10^{-4}$ M) (see e.g. Sledge et al., J. Biol. Chem. 248 (1973) 2818-2823; Hughes-Jones et al., Mol. Immunol. 16 (1979) 697-701). The binding of the multivalent C1q may be increased by antigen-based association of the immunoglobulin molecules and, thus, complement activation (affinity about $10^{-8}$ M) (see e.g. Burton et al., Mol. Immunol. 22 (1990) 161-206).

A combination of known methods could achieve analytical results comparable to those of the C1q affinity chromatography but at the expense of increased complexity and efforts.

SPR analysis of the IgG-C1q interaction provides a qualitative result indicating expected or aberrant binding properties of a sample but does neither give a hint for the cause of aberrant binding nor a quantitative estimation of the amount of antibody with aberrant binding. Mass spectrometry also does just give qualitative information of a disturbed integrity of the IgG molecule. In contrast, the C1q affinity chromatography allows analyzing the sample under appropriate physiologic conditions with an ionic strength gradient which can be adjusted if required to fine tune the separation of the different peaks found in a sample. The different peaks can be quantitated by their respective area under the curve and the eluate corresponding to each peak is amenable to secondary analysis for e.g. functionality determinations, re-chromatography or mass spectrometric analysis.

Additionally, in order to provide therapeutic regimens to treat the diversity of diseases know today and also those that will be revealed in the future a need for tailor made antibodies as well as Fc-region containing polypeptides exists.

To tailor made the C1q binding characteristics of an antibody or an Fc-part containing fusion polypeptide the residues involved in Fc-region mediated effector functions are modified and the resulting modified antibodies and fusion polypeptides have to be tested. If the required characteristics are not met the same process is performed again.

In one embodiment the Fc-region is the fraction of a full length antibody heavy chain that mediates the binding to C1q. The fraction can comprise one or two segments relating to the different interacting residues in the heavy chain constant region (especially hinge and CH2 domain).

Thus, it would be advantageous to provide a method that predicts the changes in the characteristic properties of a modified antibody based on a simple chromatographical method and which does not require in vivo studies to analyze the changes of the characteristics in the modified antibody.

It has been found that with the fusion polypeptide as reported herein as chromatography ligand it is now possible to separate, isolate and characterize with respect to their in vivo properties closely related antibody species, i.e. differing in a single or a limited number of amino acid residues, which influence the interaction with C1q.

Thus, with the method as reported herein it is possible to separate different variants of one parent antibody and to determine the specific ratio between these variants, which is not possible with the currently known methods as these only provide the sum of the modifications and not the individual species (i.e. for a mixture of parent and variant 1 and variant 2 and variant 1/2 mass spectrometry provides for the total of variant 1 comprising molecules, i.e. variants comprising a single variation (1) and also those comprising also the second variation (1/2)).

It has been found that for the given conditions a wild-type IgG1 antibody has a retention time of about 25 to 28 minutes under the conditions as outlined in the Examples provided herein.

An antibody having a modified Fc-region with reduced C1q binding has a retention time that is smaller, whereas an antibody having a modified Fc-region with enhanced C1q binding has a retention time that is bigger compared to an antibody having the parental unmodified Fc-region.

One aspect as reported herein is a fusion polypeptide according to formula I

TAG-X1-C1qA-X2-C1qB-X3-C1qC-X4 (formula I)

wherein

X1 denotes a first peptidic linker,

X2 denotes a second peptidic linker,

X3 denotes a third peptidic linker,

X4 denotes a fourth peptidic linker,

X1, X2, X3, X4 are independently of each other either present or absent,

TAG is an amino acid sequence tag,

TAG can be present or absent,

C1qA is a fragment of SEQ ID NO: 01,

C1qB is a fragment of SEQ ID NO: 03,

C1qC is a fragment of SEQ ID NO: 05, and

- denotes a peptide bond.

C1q chain A (C 1QA, Complement C1q subcomponent subunit A) has the amino acid sequence of SEQ ID NO: 01 (UniProtKB-P02745 (C1QA_HUMAN)).

C1q chain B (C1QB, Complement C1q subcomponent subunit B) has the amino acid sequence of SEQ ID NO: 03 (UniProtKB-P02746 (C1QB_HUMAN)).

C1q chain C (C1QC, Complement C1q subcomponent subunit C) has the amino acid sequence of SEQ ID NO: 05 (UniProtKB-P02747 (C1QC_HUMAN)).

C1q is composed of 18 polypeptide chains: six A-chains, six B-chains, and six C-chains. The A-, B-, and C-chains are arranged in the order A-C-B on chromosome 1 in the human genome. In contrast thereto the subunits are arranges in the order A-B-C in the fusion polypeptide as reported herein.

Each of the complement C1q subcomponent subunits comprises a collagen-like domain and a C1q domain. Between residues 4 of the collagen like domains of subunit A and B (residue 4 of SEQ ID NO: 01 and 03) a disulfide bond is formed. Between residues 4 of the collagen like domains of two C subunits (residue 4 of SEQ ID NO: 05) also a disulfide bond is formed.

| subunit | subunit length | collagen-like domain comprises residues | C1q domain comprises residues | fragment comprises residues |
|---|---|---|---|---|
| A | 223 | 9-87 | 88-223 | 90-223 |
| B | 223 | 10-59/33-87 | 90-226 | 92-223 |
| C | 217 | 4-84 | 87-217 | 89-217 |

As in the fusion polypeptide as reported herein fragments of the three subunits, which do no longer comprises the above mentioned cysteine residues, are fused, also the naturally occurring disulfide bonds can no longer be formed.

One aspect as reported herein is the use of an immobilized fusion polypeptide according to formula I TAG-X1-C1qA-X2-C1qB-X3-C1qC-X4 (formula I)

wherein
X1 denotes a first peptidic linker,
X2 denotes a second peptidic linker,
X3 denotes a third peptidic linker,
X4 denotes a fourth peptidic linker,
X1, X2, X3, X4 are independently of each other either present or absent,
TAG is an amino acid sequence tag,
TAG can be present or absent,
C1qA is a fragment of SEQ ID NO: 01,
C1qB is a fragment of SEQ ID NO: 03,
C1qC is a fragment of SEQ ID NO: 05, and
- denotes a peptide bond
as affinity chromatography ligand.

One aspect as reported herein is the use of an immobilized fusion polypeptide according to formula I TAG-X1-C1qA-X2-C1qB-X3-C1qC-X4      (formula I)

wherein
X1 denotes a first peptidic linker,
X2 denotes a second peptidic linker,
X3 denotes a third peptidic linker,
X4 denotes a fourth peptidic linker,
X1, X2, X3, X4 are independently of each other either present or absent,
TAG is an amino acid sequence tag,
TAG can be present or absent,
C1qA is a fragment of SEQ ID NO: 01,
C1qB is a fragment of SEQ ID NO: 03,
C1qC is a fragment of SEQ ID NO: 05, and
- denotes a peptide bond
as affinity chromatography ligand for the separation of antibody glycoforms.

The sum of the glycoforms of an antibody is denoted as "glycoprofile" or "glycosylation profile". These terms refer to the properties of the glycans of a glycosylated polypeptide. These properties are the glycosylation sites, or the glycosylation site occupancy, or the identity, structure, composition or quantity of the glycan and/or non-saccharide moiety of the polypeptide, or the identity and quantity of the specific glycoform.

As used herein, a "glycan" is a sugar. Glycans can be monomers or polymers of sugar residues, but typically contain at least three sugars, and can be linear or branched. A glycan may include natural sugar residues (e.g., glucose, N-acetyl glucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'-sulfo N-acetyl glucosamine, etc.). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

As used herein, the term "glycoprotein preparation" refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one of the glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform". Thus, the term "glycoform" denotes a type of polypeptide with a specific type and distribution of polysaccharides attached to it. For example, two polypeptides would be of the same glycoform if they comprise glycans with the same number, kind, and sequence of monosaccharides, i.e. have the same "glycosylation profile".

Also reported is an affinity chromatography column that comprises a matrix and matrix bound chromatographical functional groups, wherein the matrix bound chromatographical functional group comprises a fusion polypeptide according to formula I TAG-X1-C1qA-X2-C1qB-X3-C1qC-X4      (formula I)

wherein
X1 denotes a first peptidic linker,
X2 denotes a second peptidic linker,
X3 denotes a third peptidic linker,
X4 denotes a fourth peptidic linker,
X1, X2, X3, X4 are independently of each other either present or absent,
TAG is an amino acid sequence tag,
TAG can be present or absent,
C1qA is a fragment of SEQ ID NO: 01,
C1qB is a fragment of SEQ ID NO: 03,
C1qC is a fragment of SEQ ID NO: 05, and
- denotes a peptide bond.

Figure 16:
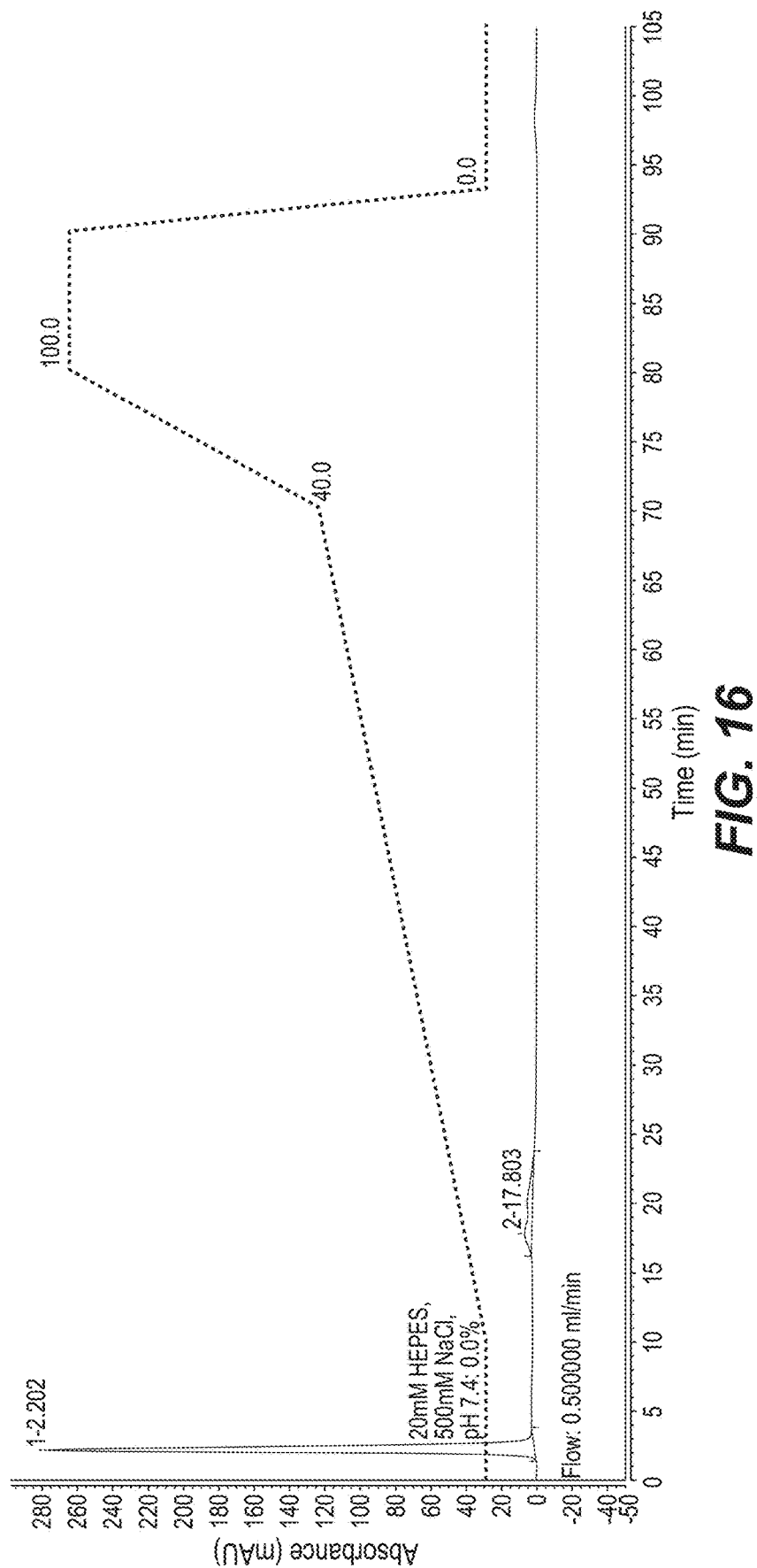
FIG. 16 Chromatogram with an Fab fragment on a C1q affinity chromatography column according to the invention.
Figure 17:
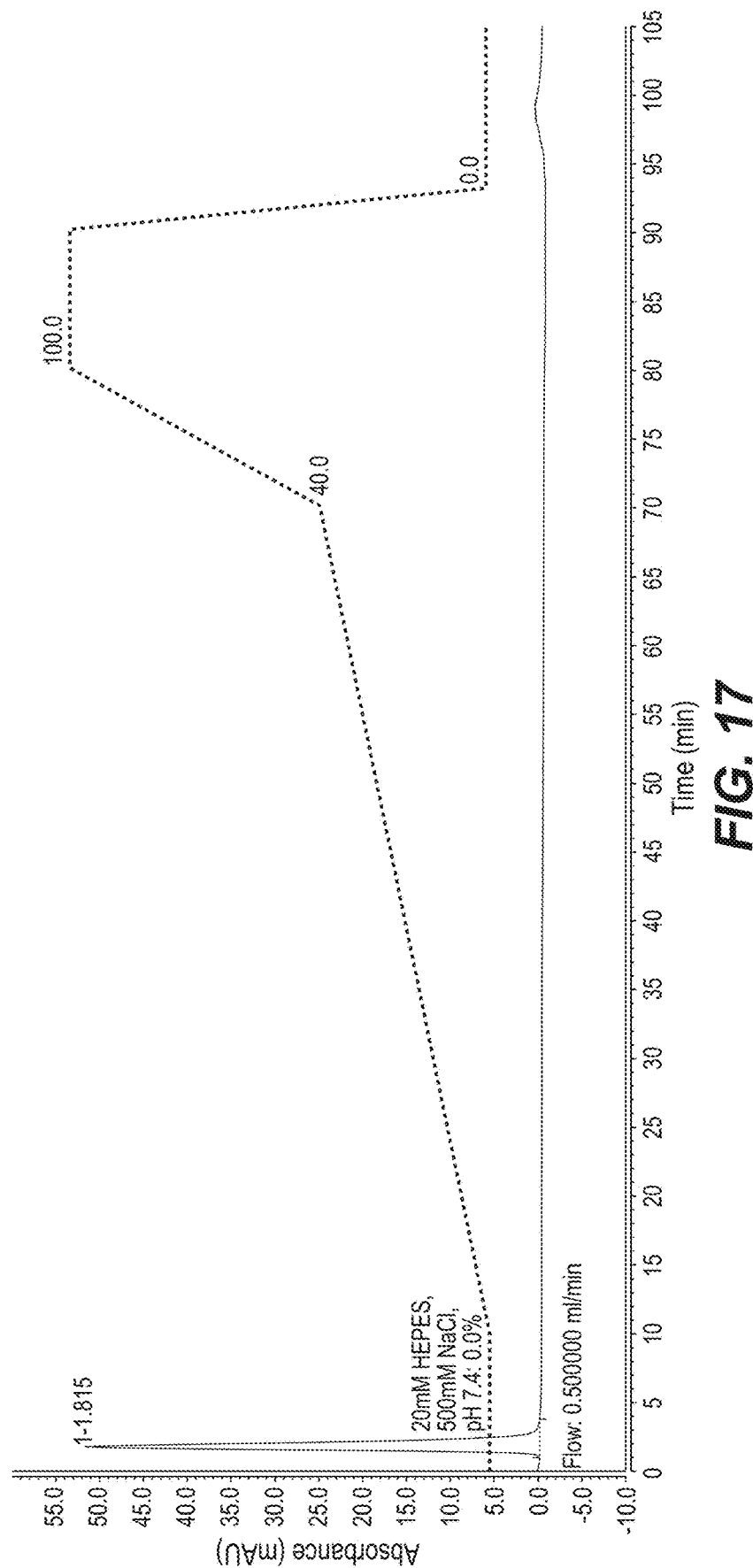
FIG. 17 Chromatogram with bovine serum albumin on a C1q affinity chromatography column according to the invention.

With such a column it it possible to specifically retain antibodies, especially full length four chain antibodies, that can interact with C1q on the column. Fab fragments and non-antibody proteins do not bind to the column (see FIGS. 16 and 17).

One aspect as reported herein is the use of an affinity chromatography column as reported herein for the determination of the relative C1q binding of an antibody by determining the ratio of the retention times of the antibody and a reference antibody. In one embodiment the reference antibody is a full length human IgG1 antibody.

One aspect as reported herein is the use of an affinity chromatography column as reported herein for separating antibodies or fusion polypeptides comprising at least a C1q-binding fragment of an Fc-region.

Herein is also reported a method for separating antibodies or fusion polypeptides comprising at least a C1q-binding fragment of an Fc-region.

In one embodiment the separating is selected from purifying, producing and analyzing.

One aspect as reported herein is the use of an affinity chromatography column as reported herein for the separation of antibodies of the IgG1 or IgG3 subclass from antibodies of the IgG2 or IgG4 subclass.

One aspect as reported herein is the use of an affinity chromatography column as reported herein for the separation of antibodies of the IgG1 subclass from antibodies of the IgG3 and/or IgG2 and/or IgG4 subclass.

Generally, starting point for the method as reported herein is a parent antibody or a parent fusion polypeptide that is characterized by binding to C1q.

One aspect as reported herein is the use of an affinity chromatography column as reported herein for screening a library of modified antibodies or modified fusion polypeptides of a parent antibody or a parent fusion polypeptide which comprise at least an C1q binding portion of an Fc-region for those modified antibodies or modified fusion polypeptides that have an altered binding affinity for C1q compared to the parent antibody or parent fusion polypeptide.

Herein is reported a method for screening a library of modified antibodies or modified fusion polypeptides of a parent antibody or a parent fusion polypeptide which comprise at least an C1q binding portion of an Fc-region for those modified antibodies or modified fusion polypeptides that have an altered binding affinity for C1q compared to the parent antibody or parent fusion polypeptide, the method comprising the following steps:
  (a) applying the individual members of the library and the parent antibody or parent fusion polypeptide to a C1q affinity chromatography column as reported herein;
  (b) recovering the individual members of the library with a ionic strength gradient and determining the individual retention times; and
  (c) selecting those antibodies or fusion polypeptides that have altered binding affinity for C1q compared to the parent antibody or parent fusion polypeptide.

Herein is reported a method for purifying an antibody or a fusion polypeptide, which comprises at least a C1q-binding part of an Fc-region, from a mixture of polypeptides, the method comprising applying the mixture to a C1q affinity column as reported herein and eluting the antibodies or the fusion polypeptide, which comprises at least a C1q binding portion of an Fc-region, with a ionic strength gradient and thereby purifying the antibody or the fusion polypeptide. In one embodiment the C1q-binding part of an Fc-region is of a human Fc-region, or a mouse Fc-region, or a cynomolgus Fc-region, or a rabbit Fc-region, or a hamster Fc-region.

One aspect as reported herein is the use of an affinity chromatography column as reported herein for identifying antibodies or fusion polypeptides that comprise at least a C1q-binding portion of an Fc-region (e.g., a constant domain of an immunoglobulin such as IgG1) which exhibit altered binding to C1q.

Herein is provided a method for identifying antibodies or fusion polypeptides that comprise at least a C1q-binding portion of an Fc-region (e.g., a constant domain of an immunoglobulin such as IgG1) which exhibit altered binding to C1q.

Such modified antibodies or fusion polypeptides show either increased or decreased binding to C1q when compared to a parent antibody or fusion polypeptide or compared to a reference antibody or reference fusion protein, and, thus, have increased or decreased CDC eliciting properties, respectively.

Fc-region variants with increased affinity for the C1q (i.e. increased retention time on a C1q affinity chromatography column compared to a parent antibody or reference antibody) are predicted to have higher CDC eliciting properties compared to those with decreased affinity for C1q. Fc-region variants with increased affinity for C1q have applications in methods of treating mammals, especially humans, where CDC of the administered antibody or fusion polypeptide is desired. Fc-region variants with decreased affinity for C1q have applications in methods of treating mammals, especially humans, where reduced CDC of the administered antibody or fusion polypeptide is desired, such as in vivo diagnostic imaging.

In one embodiment the antibody or the fusion polypeptide as reported herein comprises at least one binding site (e.g. at least one antigen binding site, or at least one receptor binding site, or at least one ligand binding site). In one embodiment, the antibody or fusion polypeptide as reported herein comprises at least two binding sites (e.g. at least two antigen binding sites, or at least two receptor binding sites, or at least two ligand binding sites, or at least one antigen binding site and at least one receptor binding site, or at least one antigen binding site and at least one ligand binding site, or at least one receptor binding site and at least one ligand binding site). In one embodiment the antibody or the fusion polypeptide as reported herein comprises three binding sites (e.g. at least three antigen binding sites, or at least three receptor binding sites, or at least three ligand binding sites, or any mixture of at least three binding sites of the before). In one embodiment the antibody or the fusion polypeptides as reported herein comprise four binding sites.

In one embodiment of all aspects as reported herein is the at least a part of an Fc-region at least a part of an Fc-region of human origin. In one embodiment of all aspects as reported herein is the C1q selected from human C1q, cynomolgus C1q, mouse C1q, rat C1q, sheep C1q, dog C1q and rabbit C1q.

In one embodiment the at least a part of an Fc-region comprises at least amino acid residues 282-340 of a CH2 domain of human origin (SEQ ID NO: 16, numbering according to Kabat). In one embodiment the at least a portion of an Fc-region comprises a complete CH2 domain (about amino acid residues 231-340 of an antibody heavy chain polypeptide Fc-region of human origin according to EU numbering according to Kabat). In one embodiment the at least a portion of an Fc-region comprises at least a CH2 domain, and at least one of a hinge region (about amino acid residues 216-230 of an antibody heavy chain polypeptide Fc-region of human origin according to EU numbering) or a CH3 domain (about amino acid residues 341-446 of an antibody heavy chain polypeptide Fc-region of human origin according to EU numbering; SEQ ID NO: 17). In one embodiment the at least a portion of an Fc-region comprises a CH2 and a CH3 domain of an antibody heavy chain of human origin. In one embodiment the at least a portion of an Fc-region comprises a hinge, a CH2 domain, and CH3 domain of an antibody heavy chain Fc-region of human origin. Fc-regions of human origin or C1q binding parts of an Fc-region of human origin portions may be derived from different isotypes, such as IgG1 (SEQ ID NO: 18) or IgG3 (SEQ ID NO: 20). In one embodiment the human isotype is IgG1.

The Fc-region of the parent antibody or comprised in the parent fusion polypeptide can be derived from different immunoglobulin molecules and/or different immunoglobulin isotypes. For example, a parent antibody or a parent fusion polypeptide may comprise a CH2 domain derived from an IgG1 isotype immunoglobulin and a hinge region derived from an IgG3 isotype immunoglobulin. Also for example, a parent antibody or a parent fusion polypeptide can comprise a hinge region derived, in part, from the IgG1 immunoglobulin subtype and, in part, from the IgG3 immunoglobulin subtype as long as these are of human origin. For example, a parent antibody or a parent fusion polypeptide can comprise a chimeric hinge region derived, in part, from an IgG1 immunoglobulin isotype and, in part, from an IgG4 immunoglobulin isotype.

The parent antibody or the parent fusion polypeptide comprises at least one Fc-region or one C1q-binding part thereof. In one embodiment the parent antibody or parent polypeptide additionally comprises at least one binding domain (in one embodiment selected from an antigen binding domain, a receptor binding domain, or a ligand binding domain). In one embodiment the parent antibody or parent fusion polypeptides comprise at least one binding domain and at least one Fc-region or one C1q-binding part thereof. In one embodiment the parent antibody or parent fusion polypeptide comprises two binding domains and two Fc-regions or two C1q-binding parts thereof.

In one embodiment the parent antibody or the parent fusion polypeptide as reported herein comprise at least one binding domain that specifically binds to a target which mediates a biological effect (in one embodiment a ligand capable of binding to a cell surface receptor or a cell surface receptor capable of binding a ligand) and mediates transmission of a negative or positive signal to a cell together with at least one Fc-region or C1q-binding part thereof. In one embodiment the parent antibody or parent fusion polypeptide comprises at least one binding domain specific for an antigen targeted for reduction or elimination (in one embodiment a cell surface antigen or a soluble antigen) and at least one Fc-region or one C1q-binding part thereof.

Antibodies specifically binding to a target can be raised in mammals by multiple subcutaneous or intraperitoneal injections of the relevant antigen (e.g. purified antigen, cells or cellular extracts comprising such antigens, or DNA encoding for such antigen) and optionally an adjuvant.

In one embodiment the antibody is a monoclonal antibody.

In one embodiment the fusion polypeptide comprises an antibody fragment (e.g. a scFv molecule, a minibody, a tetravalent minibody, or a diabody) operably linked to a C1q-binding portion. In one embodiment, the C1q-binding portion is a complete antibody heavy chain Fc-region.

In one embodiment the parent antibody is a bispecific antibody or the parent fusion polypeptide comprises a bispecific antibody or a bispecific antibody fragment.

In one embodiment the parent antibody is a chimeric antibody.

In one embodiment the parent fusion polypeptide comprises at least a C1q-binding part of an Fc-region. In one embodiment the parent fusion polypeptide comprise one or more binding domain(s) which in turn each comprise one binding site. The parent fusion polypeptide can be bispecific (with one binding site specifically binding to a first target and a second binding site specifically binding to a second target) or multivalent (with two binding sites specifically binding to the same target).

Generally, the binding domain is fused to the C-terminus or the N-terminus of the at least a C1q-binding portion of an Fc-region.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces in that a "solid support" contains at least one moiety on its surface, which is intended to interact chemically with a molecule. A solid phase may be a stationary component, such as a chip, tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, May 1 (1998) 322A-327A, which is incorporated herein by reference. In one embodiment the solid support is sepharose. In one embodiment the solid phase is a magnetic bead.

In one embodiment the conjugation of the fusion polypeptide as reported herein to the solid phase is performed by chemically binding via N-terminal and/or e-amino groups (lysine), e-amino groups of different lysins, carboxy-, sulfhydryl-, hydroxyl-, and/or phenolic functional groups of the amino acid backbone of the antibody, and/or sugar alcohol groups of the carbohydrate structure of the antibody.

In one embodiment the fusion polypeptide as reported herein is conjugated to the solid phase via a specific binding pair. In one embodiment the fusion polypeptide is conjugated to biotin and immobilization to a solid support is performed via solid support immobilized avidin or streptavidin.

In one embodiment the solid phase is a magnetic bead.

A specific binding pair (first component/second component) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc.

The recovering of antibody bound to the C1q affinity column as reported herein in the uses and methods as reported herein is by a linear gradient elution. In one embodiment the linear gradient is an ionic strength gradient or a conductivity gradient.

In principle any buffer substance can be used in the methods as reported herein.

The following exemplary data has been determined with a C1q affinity chromatography column (length: 50 mm; diameter: 5 mm; bed volume: 1 ml; 1 mg fusion protein/ml of solid phase) using a linear salt gradient (ionic strength/conductivity gradient) of Eluent A (20 mM HEPES buffer, pH 7.4) and eluent B (20 mM HEPES buffer supplemented with 500 mM NaCl, pH 7.4) according to the following Table.

TABLE

| time [min] | Eluent A [%] | Eluent B [%] |
| --- | --- | --- |
| 0 | 100 | 0 |
| 10 | 100 | 0 |
| 70 | 60 | 40 |
| 80 | 0 | 100 |
| 90 | 0 | 100 |
| 93 | 100 | 0 |
| 103 | 100 | 0 |

The retention time of antibodies of different IgG subclasses obtained with the C1q affinity chromatography column as reported herein using the elution method as outlined above is shown in the following table (see also FIG. 1).

TABLE

| subclass | retention time [min] |
|---|---|
| IgG1 | 26.5 |
| IgG3 | 37.5 |
| IgG4 | 20.0 |

Figure 8A:
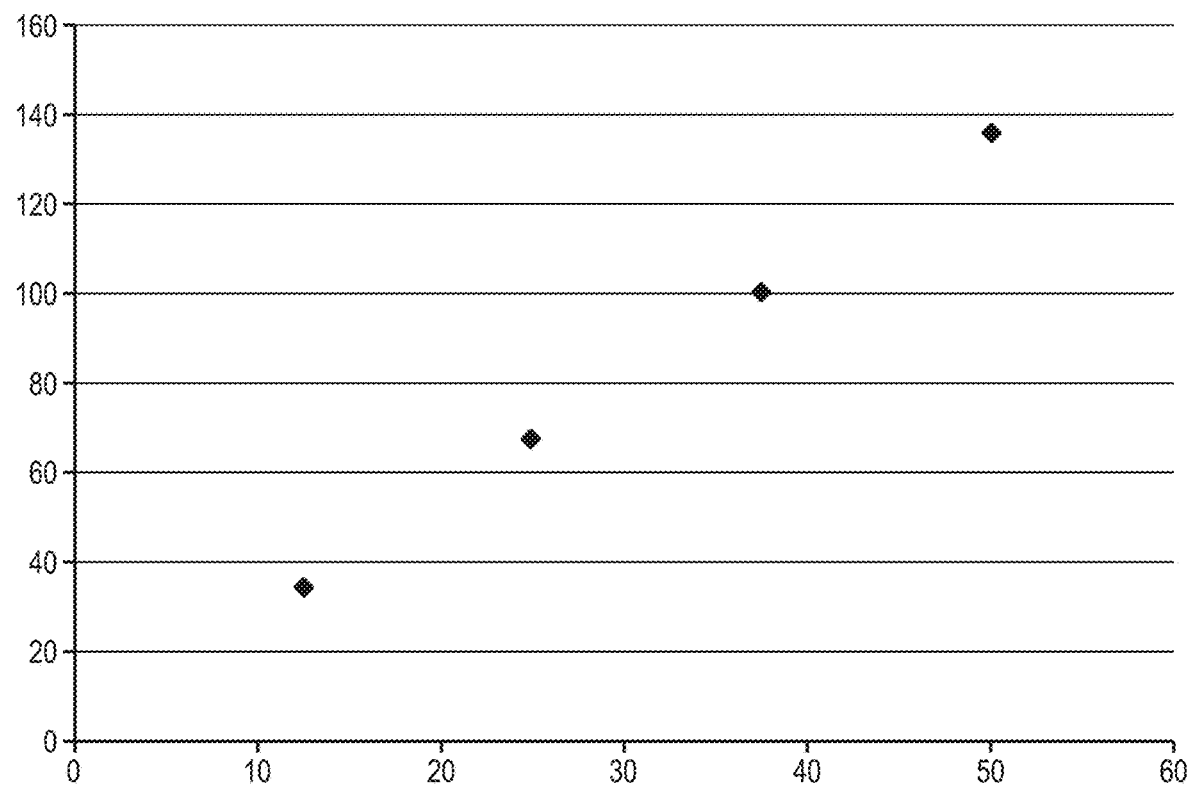
FIGS. 8A-8B Relationship of column loading (μg/ml phase/3 mg fusion polypeptide; x-axis) and detected peak area (mAus; y-axis) for an antibody of the IgG1 class (FIG. 8A) and IgG4 class (FIG. 8B).
Figure 8B:
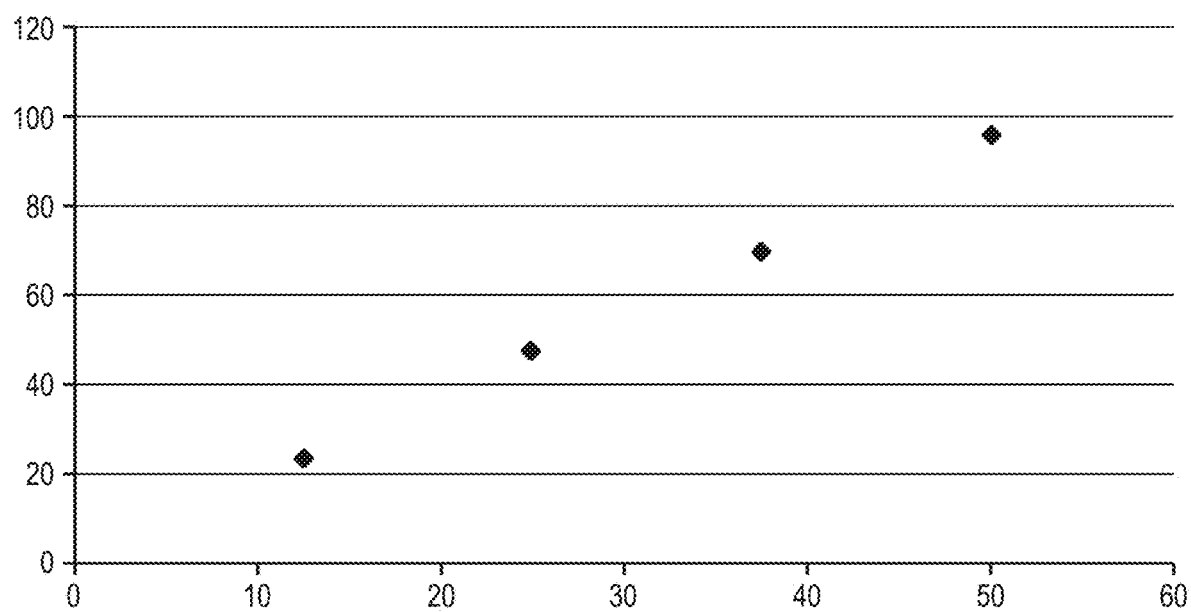
Figure 9:
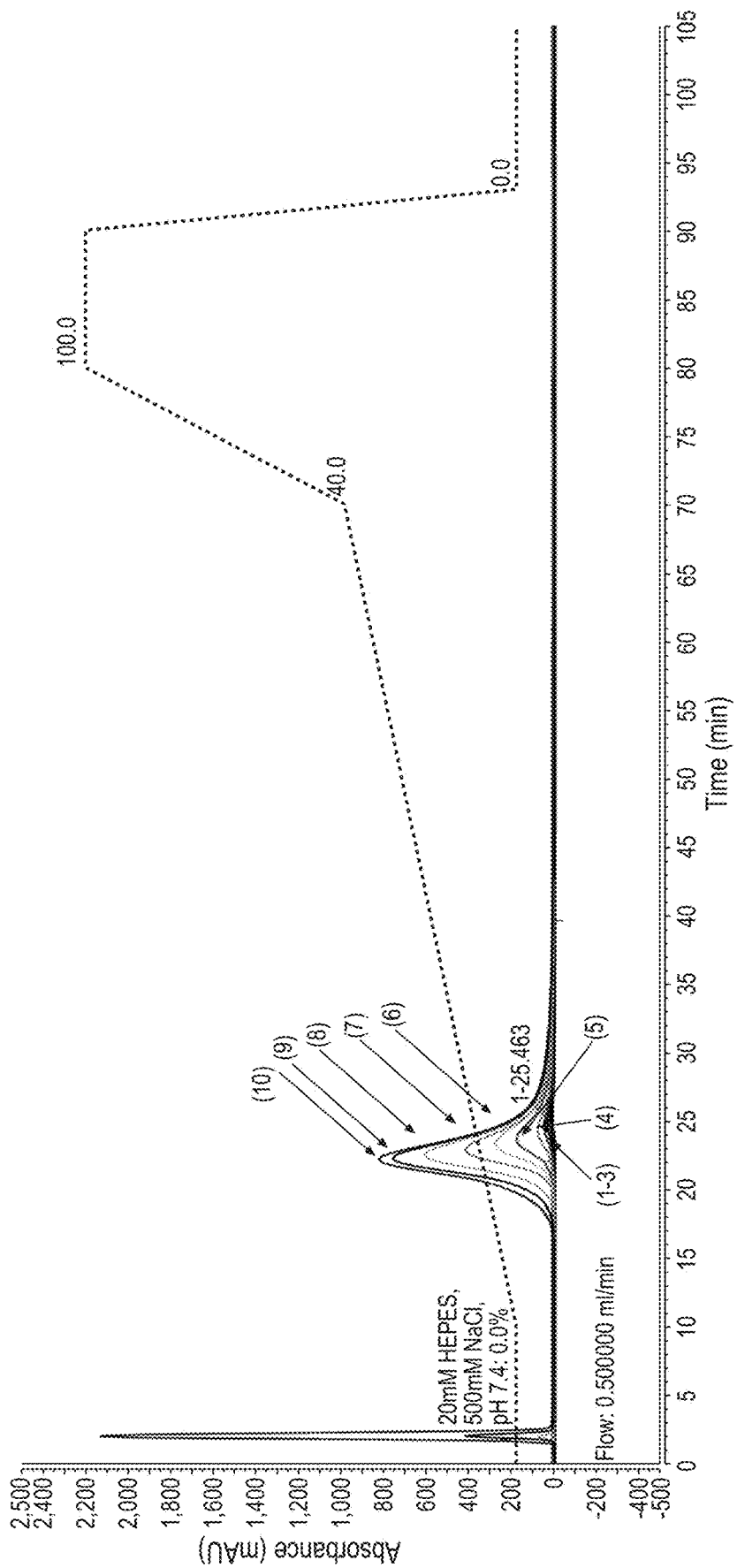
FIG. 9 Overlay of exemplary chromatograms of an antibody of the IgG1 subclass with 25 μg load (1), 50 μg load (2), 75 μg load (3), 125 μg load (4), 250 μg load (5), 375 μg load (6), 500 μg load (7), 750 μg load (8), 1000 μg load (9) and 1500 μg load (10).
Figure 10:
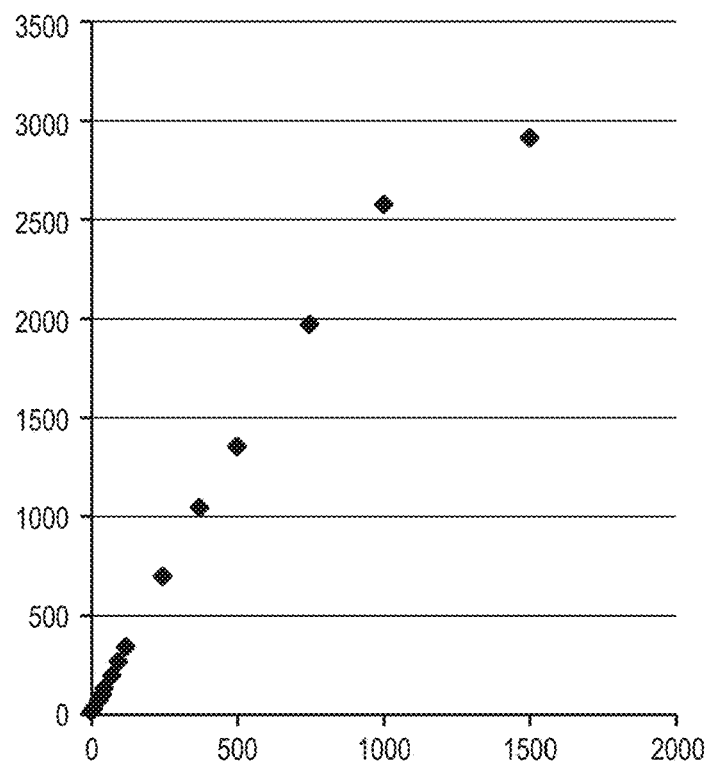
FIG. 10 Relationship of column loading (μg/ml phase/3 mg fusion polypeptide; x-axis) and detected peak area (mAus; y-axis) for an antibody of the IgG1 class up to 1500 μg load per 3 mg of fusion polypeptide according to the invention per ml of solid phase.
Figure 11:
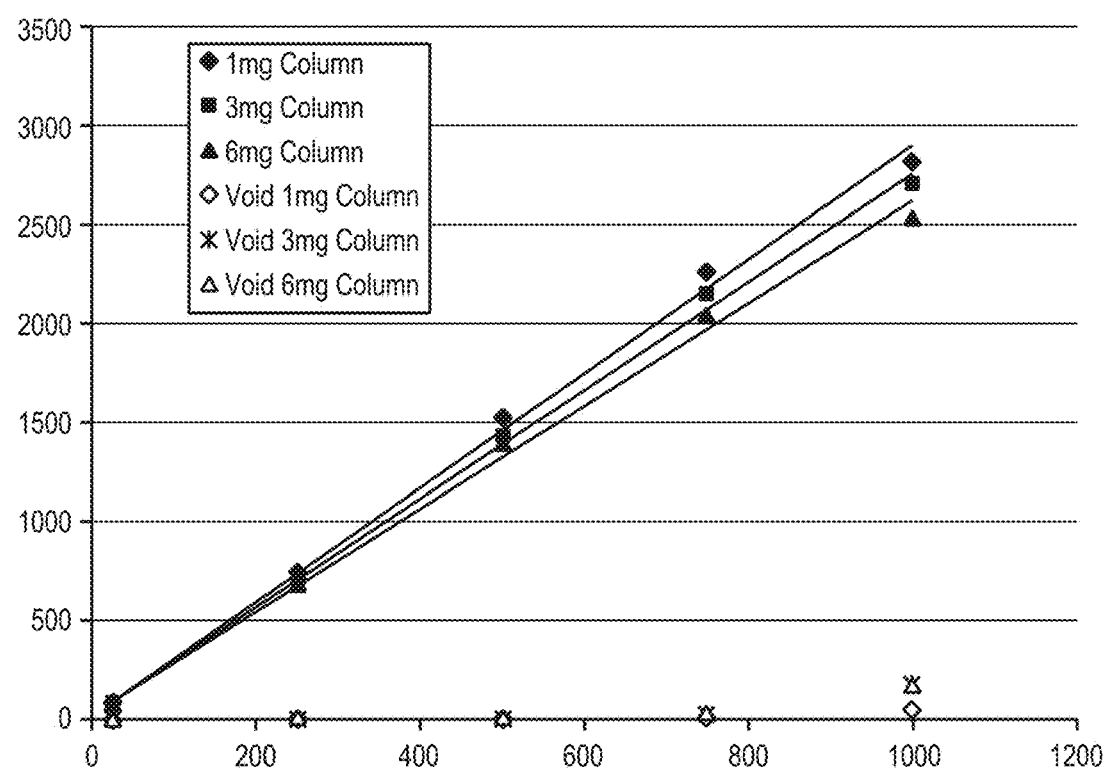
FIG. 11 Relationship of column loading (μg/ml phase/X mg fusion polypeptide; x-axis; diamond=1 mg/ml, square=3 mg/ml, triangle=6 mg/ml) and detected peak area (mAus; y-axis) for an antibody of the IgG1 class up to 1500 μg load per 3 mg of fusion polypeptide according to the invention per ml of solid phase.

From FIG. 8 a linear relationship between column loading with an antibody of the IgG1 or IgG4 class an detected peak area can be seen. In FIG. 9 the overlay of chromatograms obtained on the same C1q column but with different loading is shown. A linearity can be observed until a loading of 1000 µg/1 ml of column material with 3 mg fusion protein as reported herein conjugated/immobilized per ml of column material (see FIG. 10). This linearity can be observed between 1 mg/ml and 6 mg/ml fusion protein immobilized per ml of column material/solid phase (see FIG. 11). Thus, in one embodiment the affinity chromatography with a fusion polypeptide as reported herein has a loading capacity of up to 1000 µg/1-6 mg fusion polypeptide/1 ml solid phase.

Figure 12:
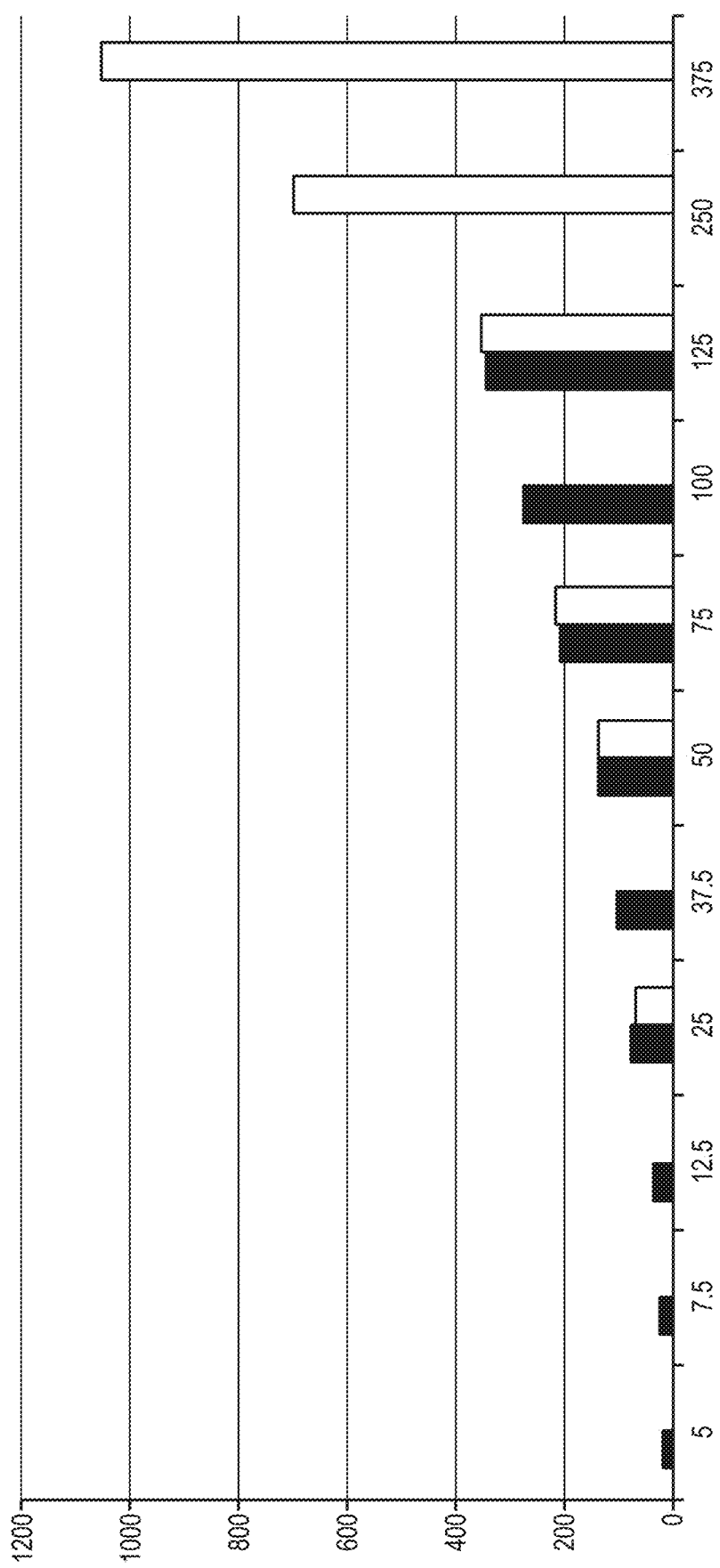
FIG. 12 Elution peak area (y-axis; mAus) in relation to loading (x-axis; g) of an antibody of the IgG1 class depending on the concentration of the loading solution (left bar: 0.5 μg/ml; right bar 5 mg/ml) on a affinity column with the fusion protein as reported herein as affinity ligand with 3 mg fusion protein per ml of column material immobilized.

The performance of the column has been found to be independent of the concentration of the loading solution. From FIG. 12 it can be seen that independent of the concentration of the loading solution the same peak area is obtained. That is, sample concentration does not affect the signal obtained.

In one embodiment the substances bound to the C1q affinity chromatography column are eluted by a linear ionic strength or conductivity gradient, wherein the column is equilibrated and washed after the application of the solution comprising the substances to be analyzed/separated/purified with a first solution, and the substances are eluted by applying a linearly changing mixture of said first solution and a second solution with increased ionic strength or conductivity.

Figure 13:
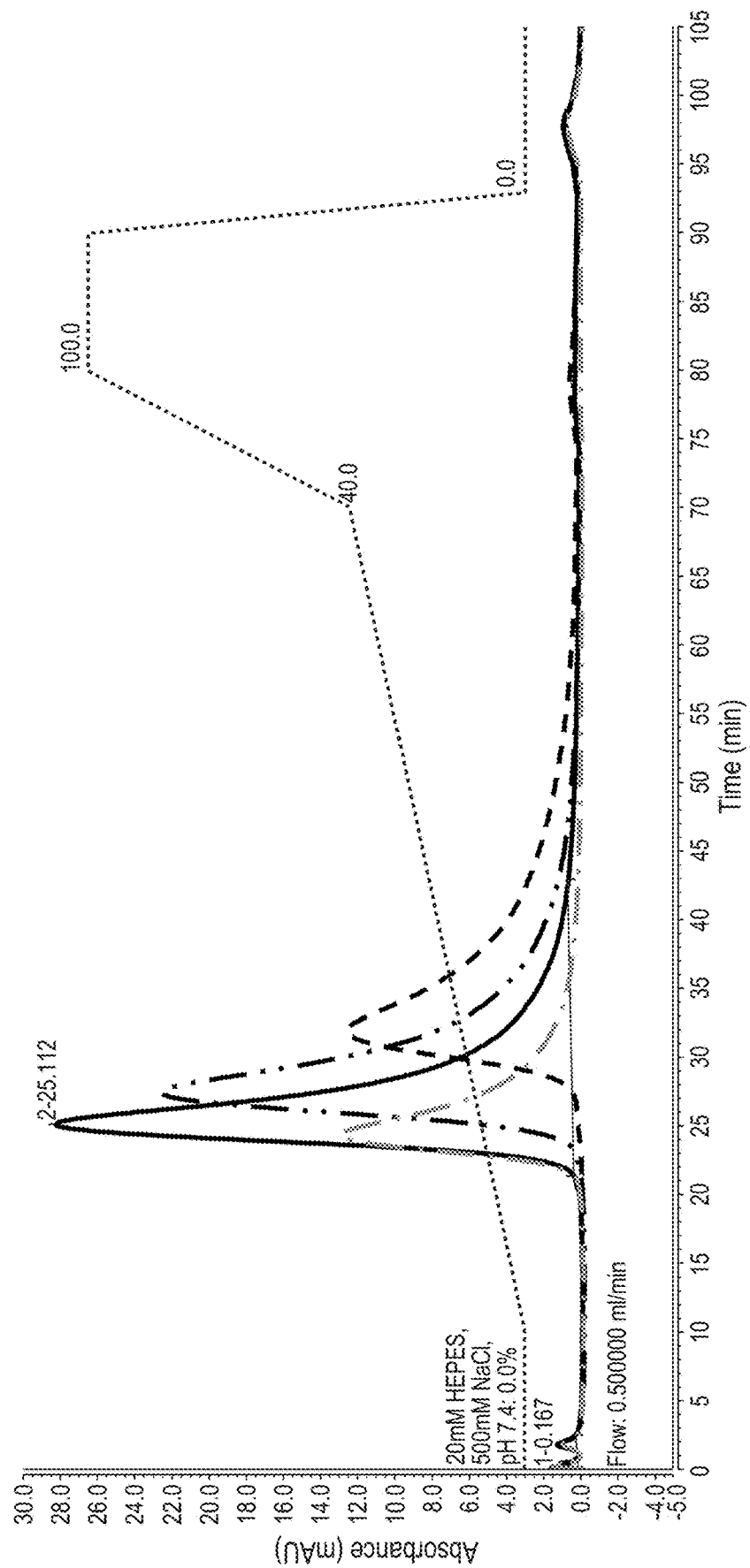
FIG. 13 Overlay of exemplary chromatograms for elution of an antibody of the IgG1 class (50 μg loading/ml of column material) with different linear gradients from 0% 20 mM HEPES buffer pH 7.4 to 20%, 30%, 40% or 50% 20 mM HEPES buffer pH 7.4 with 500 mM sodium chloride.

Depending on the slope of the gradient different retention times can be adjusted (see FIG. 13).

In one embodiment the first solution and the second solution are buffered solutions (i.e. the first solution and the second solution comprise a buffer substance).

In one embodiment a pharmaceutically acceptable buffer substance is used, such as e.g. phosphoric acid or salts thereof, acetic acid or salts thereof, citric acid or salts thereof, morpholine, 2-(N-morpholino) ethanesulfonic acid (MES) or salts thereof, histidine or salts thereof, glycine or salts thereof, tris (hydroxymethyl) aminomethane (TRIS) or salts thereof, (4-(2-hydroxyethyl)-1-piperazineethanesulfonic acid (HEPES) or salts thereof.

In one embodiment the buffer substance is selected from morpholine, 2-(N-morpholino) ethanesulfonic acid (MES) or salts thereof, tris (hydroxymethyl) aminomethane (TRIS) or salts thereof, (4-(2-hydroxyethyl)-1-piperazineethanesulfonic acid (HEPES) or salts thereof.

In one embodiment the buffer substance has a concentration of from 10 mM to 500 mM. In one embodiment the buffer substance has a concentration of from 10 mM to 300 mM. In one embodiment the buffer substance has a concentration of from 10 mM to 250 mM. In one embodiment the buffer substance has a concentration of from 10 mM to 200 mM. In one embodiment the buffer substance has a concentration of from 10 mM to 150 mM. In one embodiment the buffer substance has a concentration of from 10 mM to 100 mM. In one embodiment the buffer substance has a concentration of from 15 mM to 50 mM. In one embodiment the buffer substance has a concentration of about 20 mM. In one embodiment the buffer substance has a concentration of from 100 mM to 150 mM In one embodiment the buffer substance in the first solution and the buffer substance in the second solution are the same buffer substance.

In one embodiment the buffer substance in the first solution and the buffer substance in the second solution are different buffer substances.

In one embodiment the buffer substance in the first solution and the buffer substance in the second solution have the same concentration.

Figure 15:
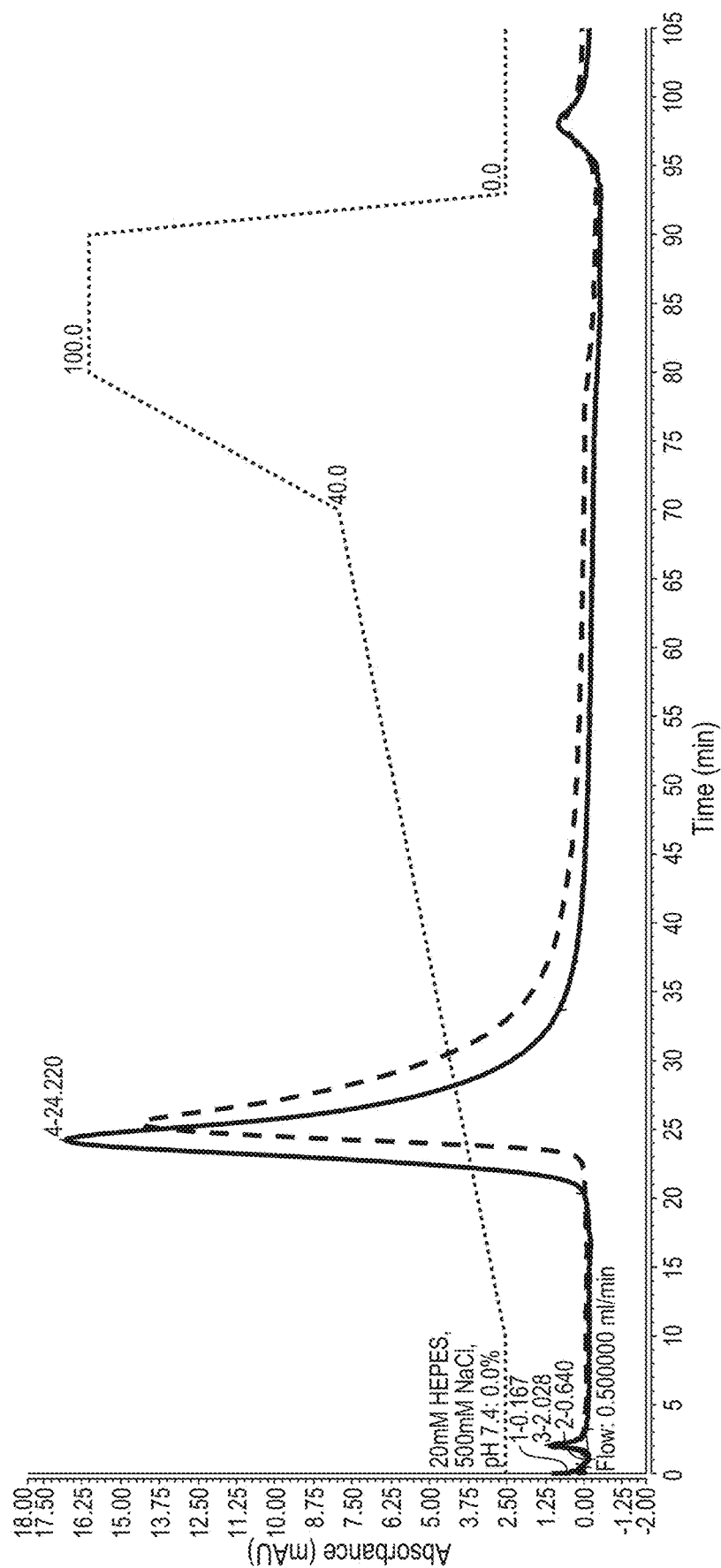
FIG. 15 Overlay of exemplary chromatograms for elution of an antibody of the IgG1 class (25 μg loading/ml of column material) with the same linear gradient from 0% 20 mM HEPES buffer pH 7.4 to 40% 20 mM HEPES buffer pH 7.4 with 500 mM sodium chloride (dashed line) or 500 mM potassium chloride (solid line).

The counter ion of the buffer salt has only a minor influence on the retention time (see FIG. 15).

In one embodiment the first and/or second solution comprise an additional salt. In one embodiment the additional salt is selected from sodium chloride, sodium sulphate, potassium chloride, potassium sulfate, sodium citrate, or potassium citrate. In one embodiment comprises the buffered solution of from 50 mM to 1000 mM of the additional salt. In one embodiment the solution(s) comprise(s) of from 50 mM to 750 mM of the additional salt. In one embodiment the solution(s) comprise(s) of from 50 mM to 500 mM of the additional salt. In one embodiment the solution(s) comprise(s) of from 50 mM to 750 mM of the additional salt. In one embodiment the buffered solution(s) comprise(s) about 50 mM to about 300 mM of the additional salt.

In one embodiment the first and/or second solution comprises sodium chloride. In one embodiment the first and/or second solution comprises of about 50 mM to about 750 mM sodium chloride.

In one embodiment the first solution and the second solution comprises sodium chloride. In one embodiment the first solution comprises about 0 mM to about 15 mM sodium chlorid and the second solution comprises about 100 mM to about 1000 mM sodium chloride, preferably about 100 mM to about 500 mM sodium chloride.

One exemplary preferred first solution comprises 20 mM HEPES, adjusted to pH 7.4.

One exemplary preferred second solution comprises 20 mM HEPES and 500 mM NaCl, adjusted to pH 7.4.

Figure 14:
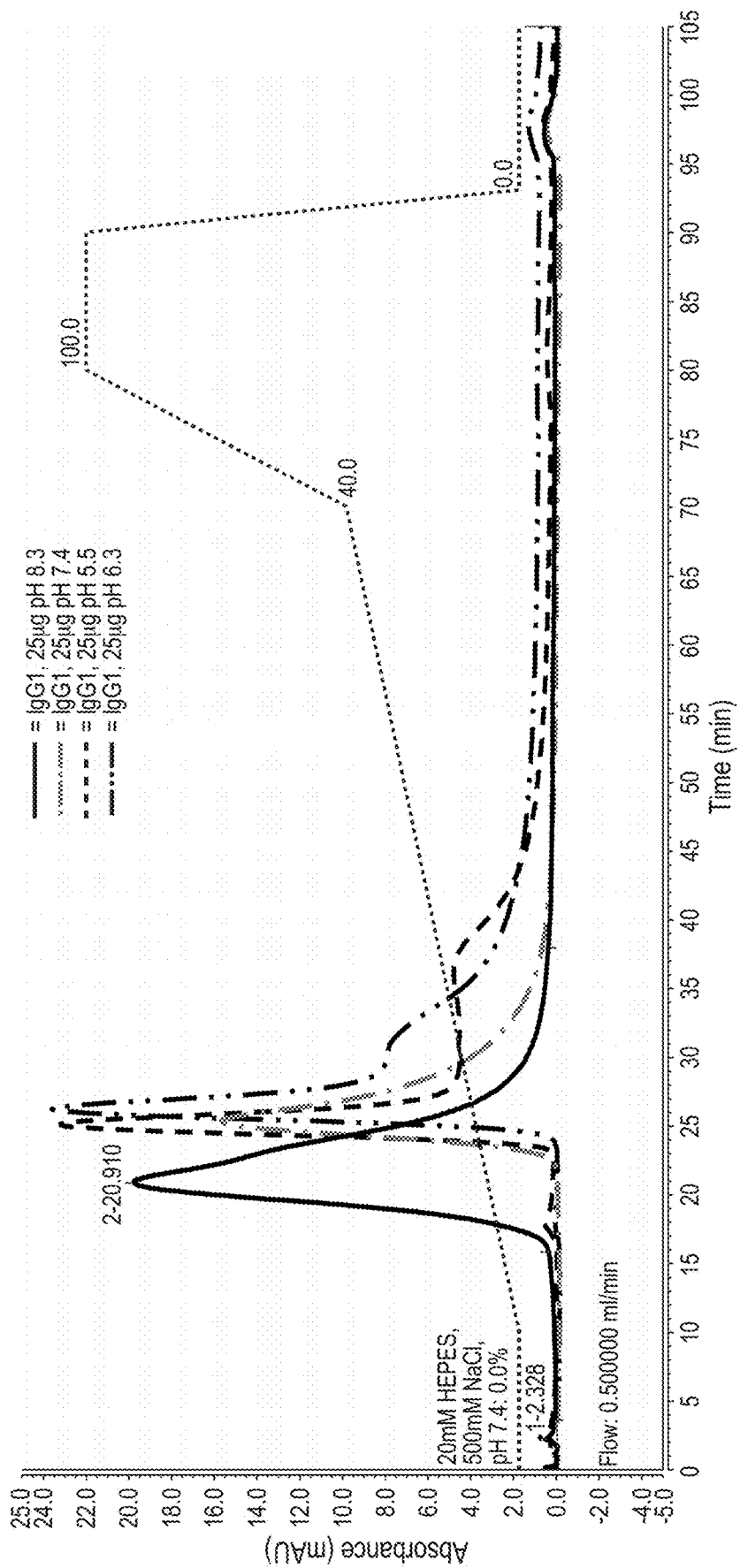
FIG. 14 Overlay of exemplary chromatograms for elution of an antibody of the IgG1 class (25 μg loading/ml of column material) with the same linear gradient from 0% 20 mM HEPES buffer pH 7.4 to 40% 20 mM HEPES buffer with 500 mM sodium chloride at pH values of 8.3, 7.4, 6.3 and 5.5.

As the C1q binding is pH dependent the pH of the first and second solution influences the elution profile, i.e. the retention time and peak shape (see FIG. 14).

The affinity chromatography material with the fusion polypeptide as reported herein as affinity chromatography ligand bound to a matrix can be used for the analysis/separation of the individual glycoforms of an antibody.

Figure 2:
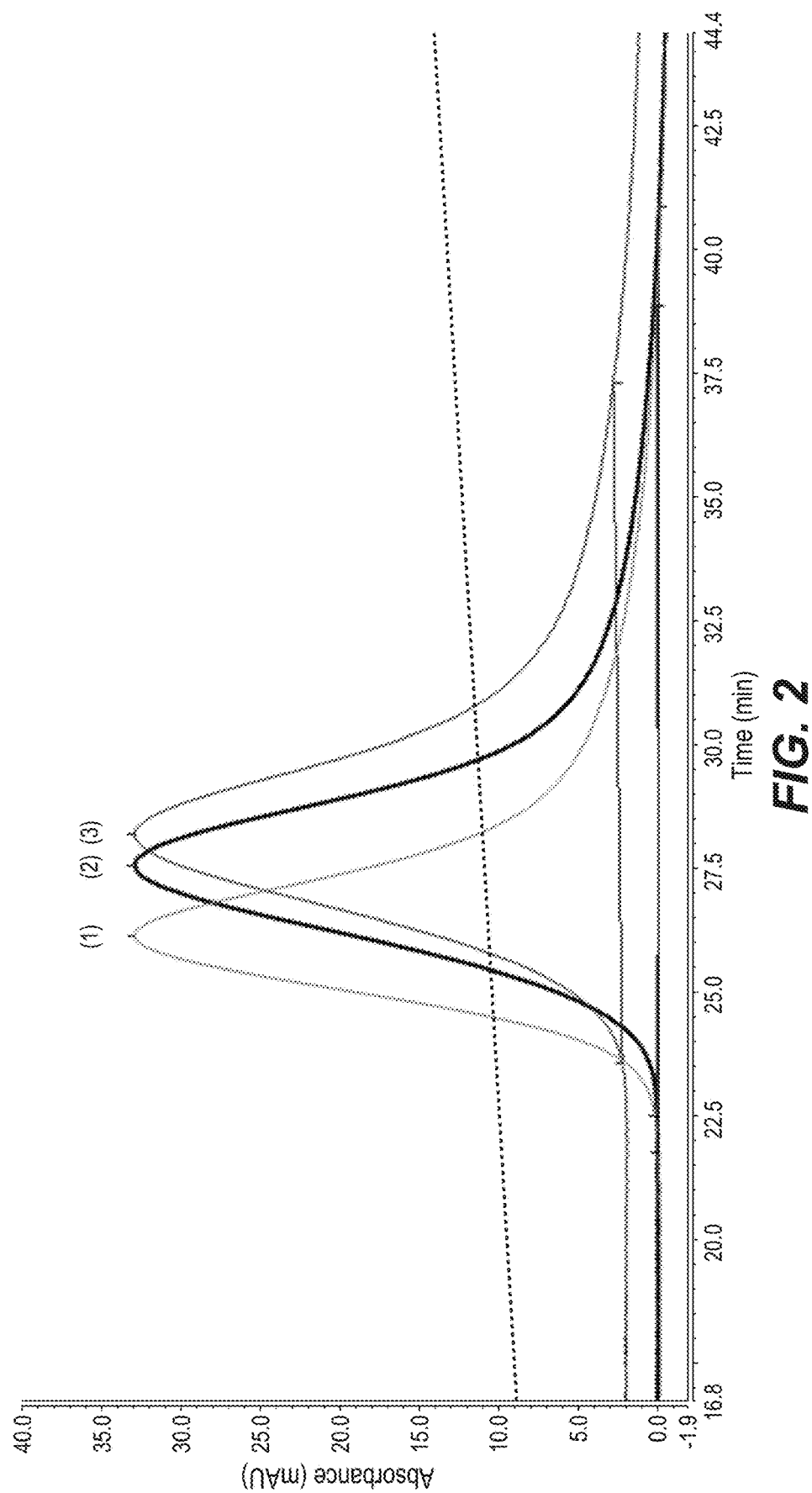
FIG. 2 Overlay of exemplary chromatograms of an antibody of the IgG1 subclass in deglycosylated form (1), in G(0) form (2), and in G(2) form (3). The dotted line represents the course of the ionic strength gradient.

For example, in the following Table the retention time differences of the same anti-EGFR antibody of the IgG1 subclass in deglycosylated form, as G(0) form and as G(2) are given. The respective chromatogram is shown in FIG. 2.

TABLE

| glycoform | retention time [min] |
|---|---|
| deglycosylated | 26.15 |
| G(0) form | 27.59 |
| G(2) form | 28.23 |

Figure 3:
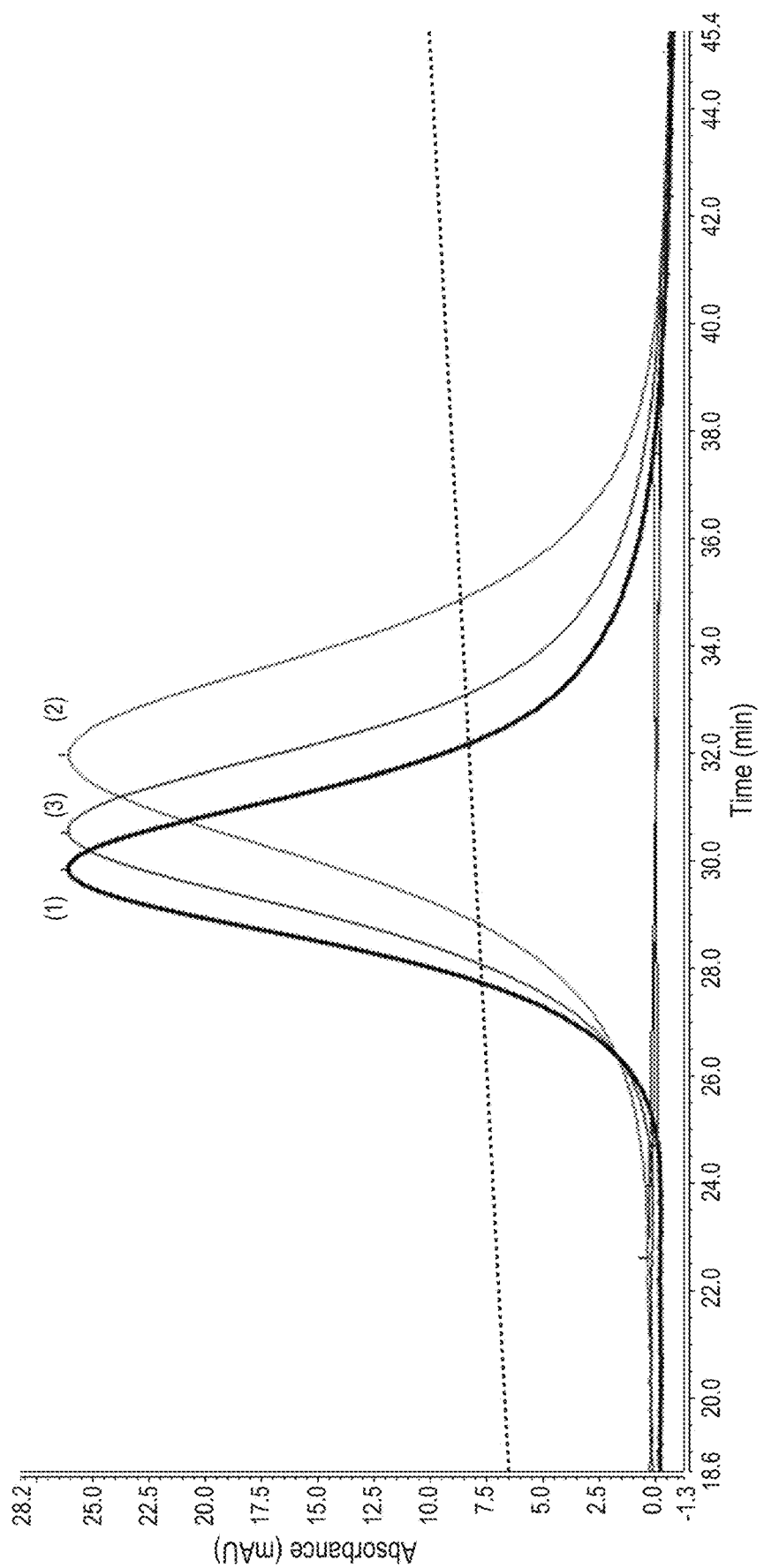
FIG. 3 Overlay of exemplary chromatograms of an antibody of the IgG1 subclass in degalactosylated form (1), in fully sialidated form (2) and in fully galactosylated form (3). The dotted line represents the course of the ionic strength gradient.

For example, in the following Table the retention time differences of the same anti-CD20 antibody of the IgG1 subclass in degalactosylated form, in fully sialidated form and in fully galactosylated form are given. The respective chromatogram is shown in FIG. 3.

TABLE

| glycoform | retention time [min] |
|---|---|
| degalactosylated | 29.86 |
| fully sialidated | 31.99 |
| fully galactosylated | 30.55 |

Figure 4:
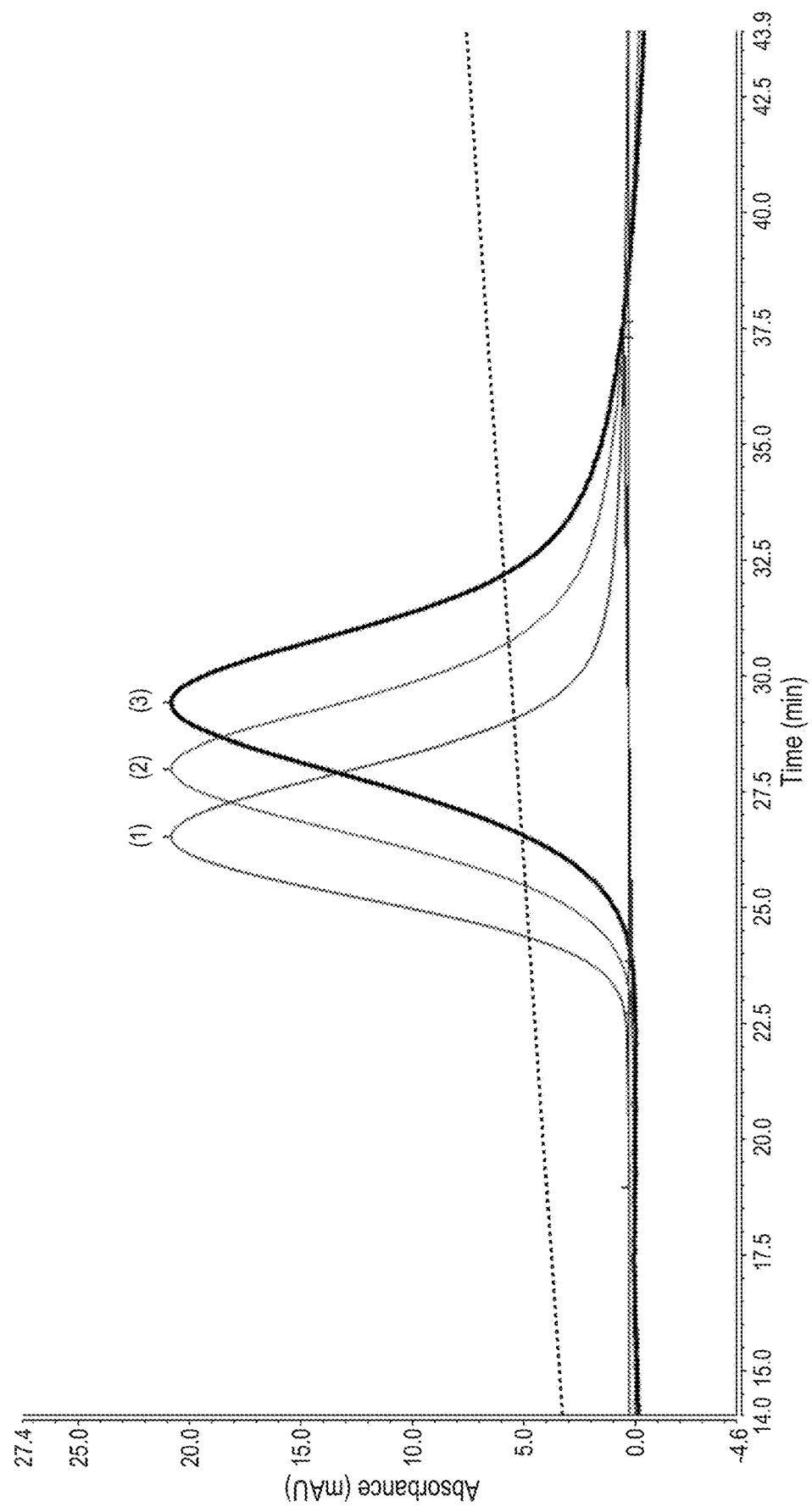
FIG. 4 Overlay of exemplary chromatograms of an antibody of the IgG1 subclass in wild-type glycosylated form (1), in fully sialilated on Man3-GlcNac-NANA/NGNA form (2), and in fully sialilated on Man6-GlcNac-NANA/NGNA form (3). The dotted line represents the course of the ionic strength gradient.

For example, in the following Table the retention time differences of the same IgG1 antibody in CHO-produced form, fully sialilated on Man3-GlcNac-NANA/NGNA and fully sialilated on Man6-GlcNac-NANA/NGNA are given. The respective chromatogram is shown in FIG. 4.

TABLE

| antibody glycosylation form | retention time [min] |
|---|---|
| wild-type as produced in CHO | 26.48 |
| fully sialilated on Man3-GlcNac-NANA/NGNA | 27.93 |
| fully sialilated on Man6-GlcNac-NANA/NGNA | 29.35 |

To show that with the fusion polypeptide as affinity chromatography ligand also closely related antibodies of different allotype can be analyzed the antibody pair Briakinumab (Ozespa™) and Ustekinumab (Stelara™) was used as a model system. Both Briakinumab and Ustekinumab are fully human monoclonal IgG1 antibodies. They bind to the same human p40-subunit of interleukin 12 (IL-12) and interleukin 23 (IL-23) (Gandhi, M., et al., Semin. Cutan. Med. Surg. 29 (2010) 48-52) and they are not cross-reactive to the corresponding mouse IL-12 and IL-23 (Luo, J., et al., J. Mol. Biol. 402 (2010) 797-812; Traczewski, P. and Rudnicka, L., BioDrugs. 26 (2012) 9-20). Briakinumab and Ustekinumab are an IgG1K antibody with variable heavy and light chain domains of the VH5 and Vκ1D germline families and an IgG1λ antibody with variable heavy and light chain domains of the VH3 and Vλ1 germline families, respectively. In addition to different variable domains, Briakinumab and Ustekinumab show differences in several allotype-specific amino acids in the constant domains.

Figure 5:
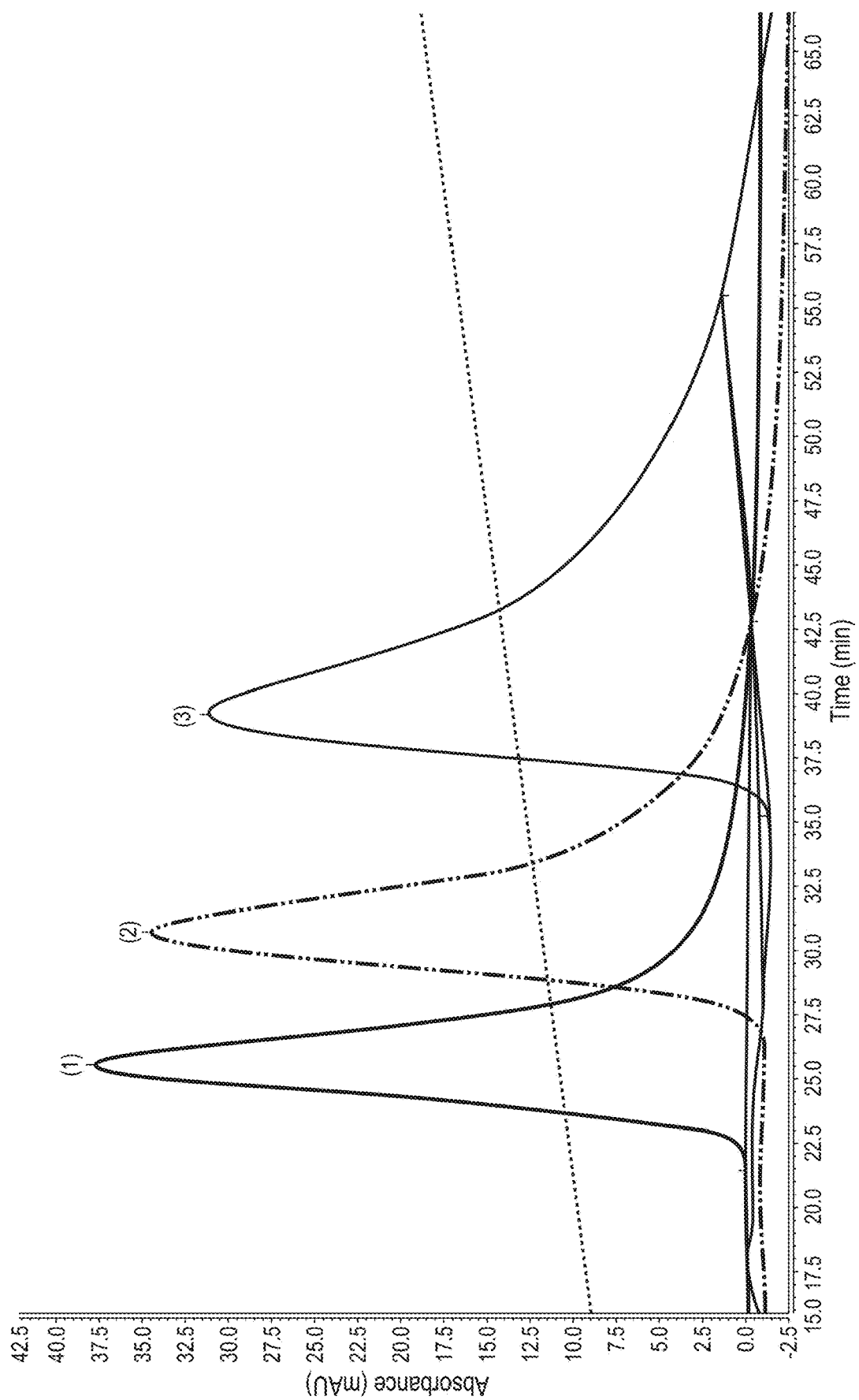
FIG. 5 Overlay of exemplary chromatograms of an antibody of the IgG1 subclass (1), Briakinumab (2) and Ustekinumab (3). The dotted line represents the course of the ionic strength gradient FIG. 6 SPR sensogram of immobilized C1q binding to Fab-complexed antibody.

In the following Table the retention time differences for an anti-IgG1 reference antibody, Briakinumab and Ustekinumab are given. The respective chromatogram is shown in FIG. 5.

TABLE

| antibody | retention time [min] |
|---|---|
| antibody of IgG1 subclass | 25.52 |
| Briakinumab | 30.66 |
| Ustekinumab | 39.13 |

In general the retention time in the methods and uses as reported herein is depending on steepness of the ionic strength/conductivity gradient and the employed salt concentration. The wild-type antibody is used as reference and a weaker binding is indicated by a shorter retention time (=earlier elution) whereas a stronger binding is indicated by a longer retention time (=later elution).

In one embodiment the fusion polypeptide is mono-biotinylated.

A chromatography material comprising a fusion polypeptide as reported herein as affinity ligand can be used for the isolation/separation of antibody fragments and, thus, provides for an alternative to conventional Protein A affinity chromatography. In addition by using the chromatography material as reported herein the separation can be effected at more physiological conditions, such as pH value, compared to conventional Protein A affinity chromatography.

The chromatography material comprising a fusion polypeptide as reported herein as ligand can be used for the determination/separation/enrichment of antibody species comprising modifications such as e.g. glycosylation. The chromatography material comprising a fusion polypeptide as reported herein as ligand can be used depending on the chosen gradient (start/end ionic strength/conductivity) for the enrichment of certain antibody species.

The chromatography material comprising a fusion polypeptide as reported herein can be used for the isolation of amino acid modifications. The chromatography material comprising a fusion polypeptide as reported herein as ligand can be used for the isolation/separation of bispecific antibody mispairings such as hole-hole dimers and half antibodies.

Figure 7:
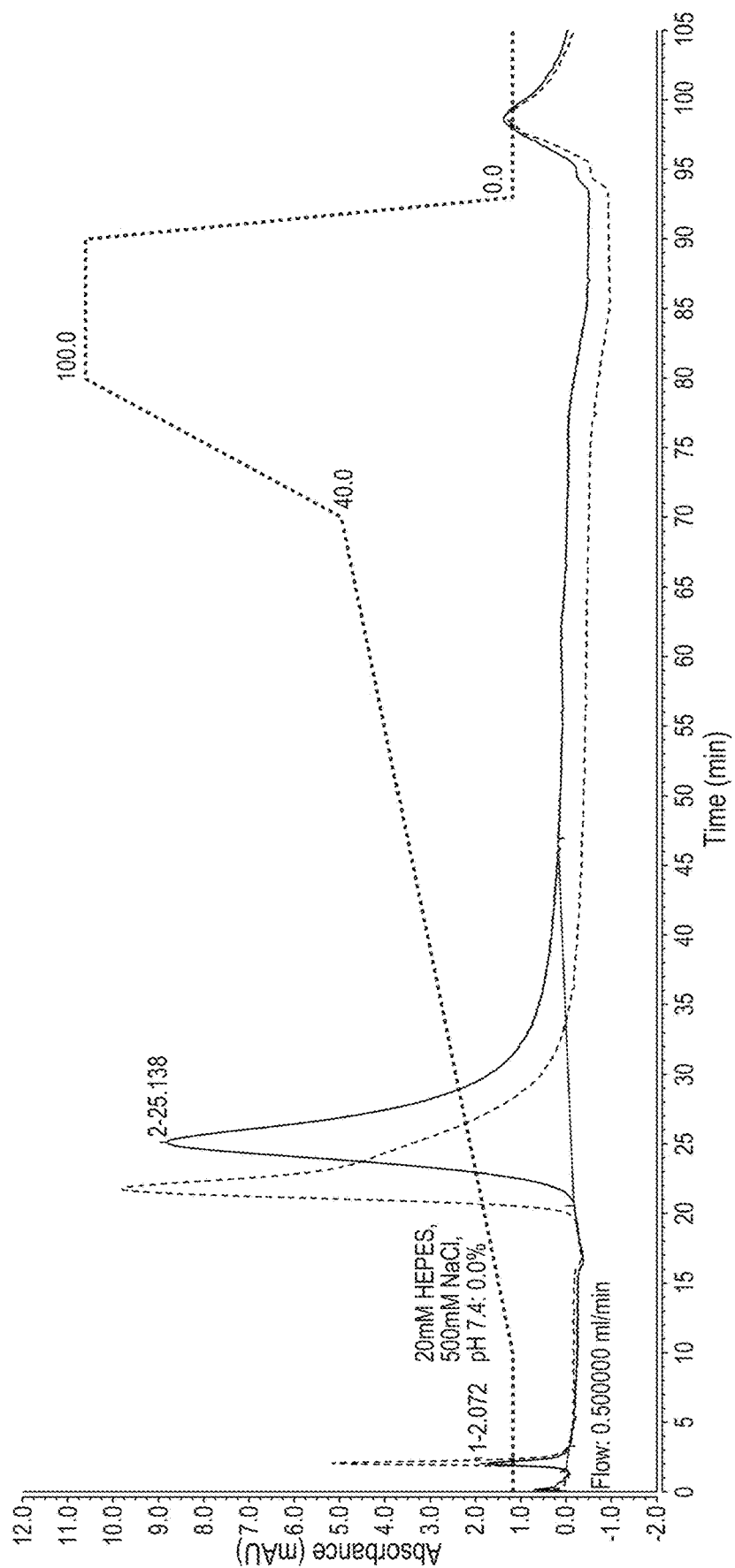
FIG. 7 Overlay of exemplary chromatograms of an antibody of the IgG1 subclass on a blank column (dashed line), i.e. a column comprising only the matrix but no ligand, and a C1q column (solid line), i.e. a column comprising the same matrix as the blank column but this time the C1q fusion polypeptide according to the invention is conjugated thereto as affinity ligand.

In FIG. 7 an overlay of exemplary chromatograms of an antibody of the IgG1 (25 µg load) subclass on a blank column, i.e. on a column comprising only the matrix/solid phase but no affinity ligand conjugated thereto, and a C1q column, i.e. on a column comprising the same matrix as the blank column before but this time the C1q fusion polypeptide according to the invention is conjugated thereto as affinity ligand. It can be seen that with the C1q affinity column a retention of the antibody can be effected.

Figure 18:
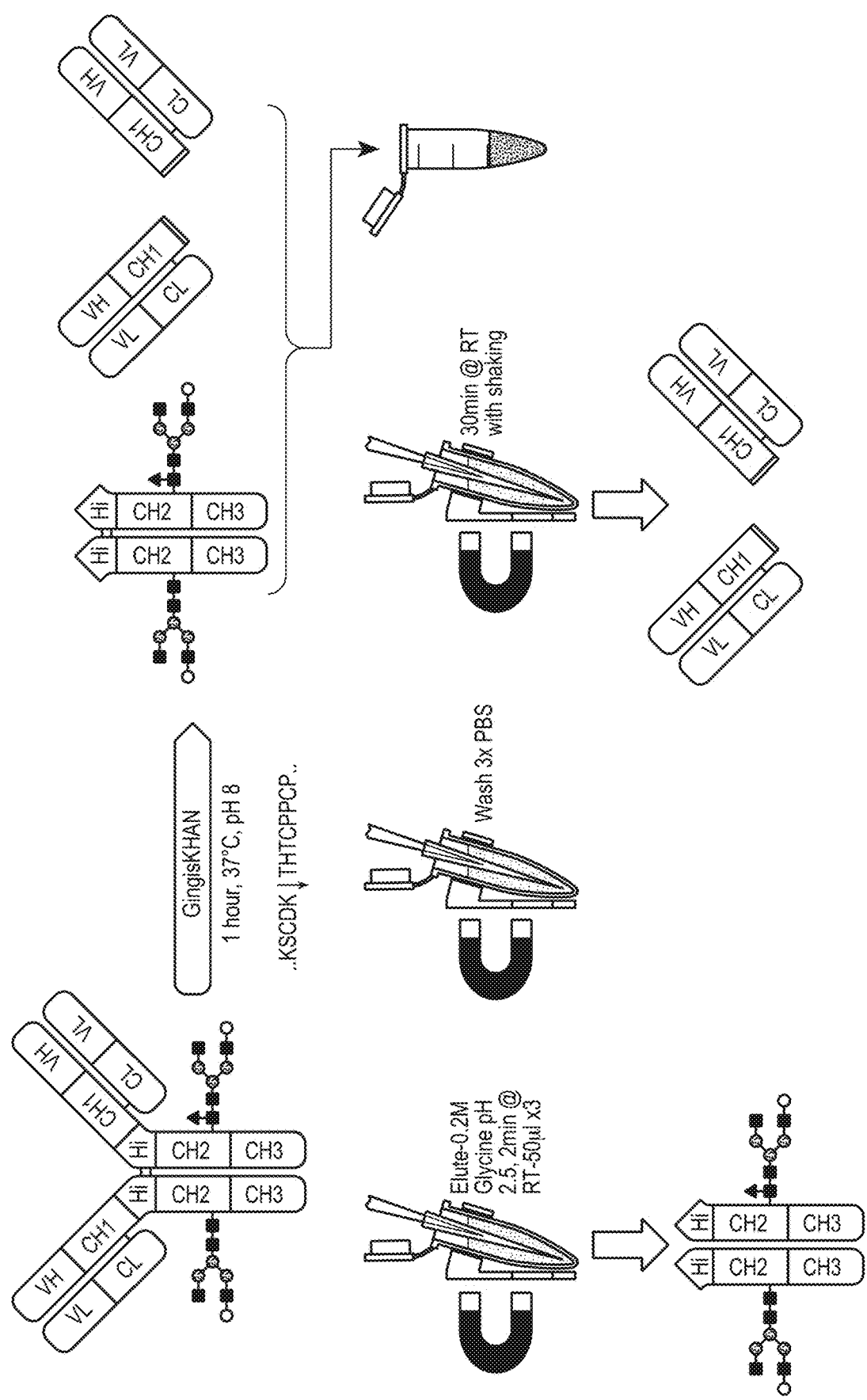
FIG. 18 Separation of antibody Fab fragment and Fc-region obtained by enzymatic cleavage of a full length antibody using the fusion protein according to the invention immobilized on magnetic beads.
Figure 19:
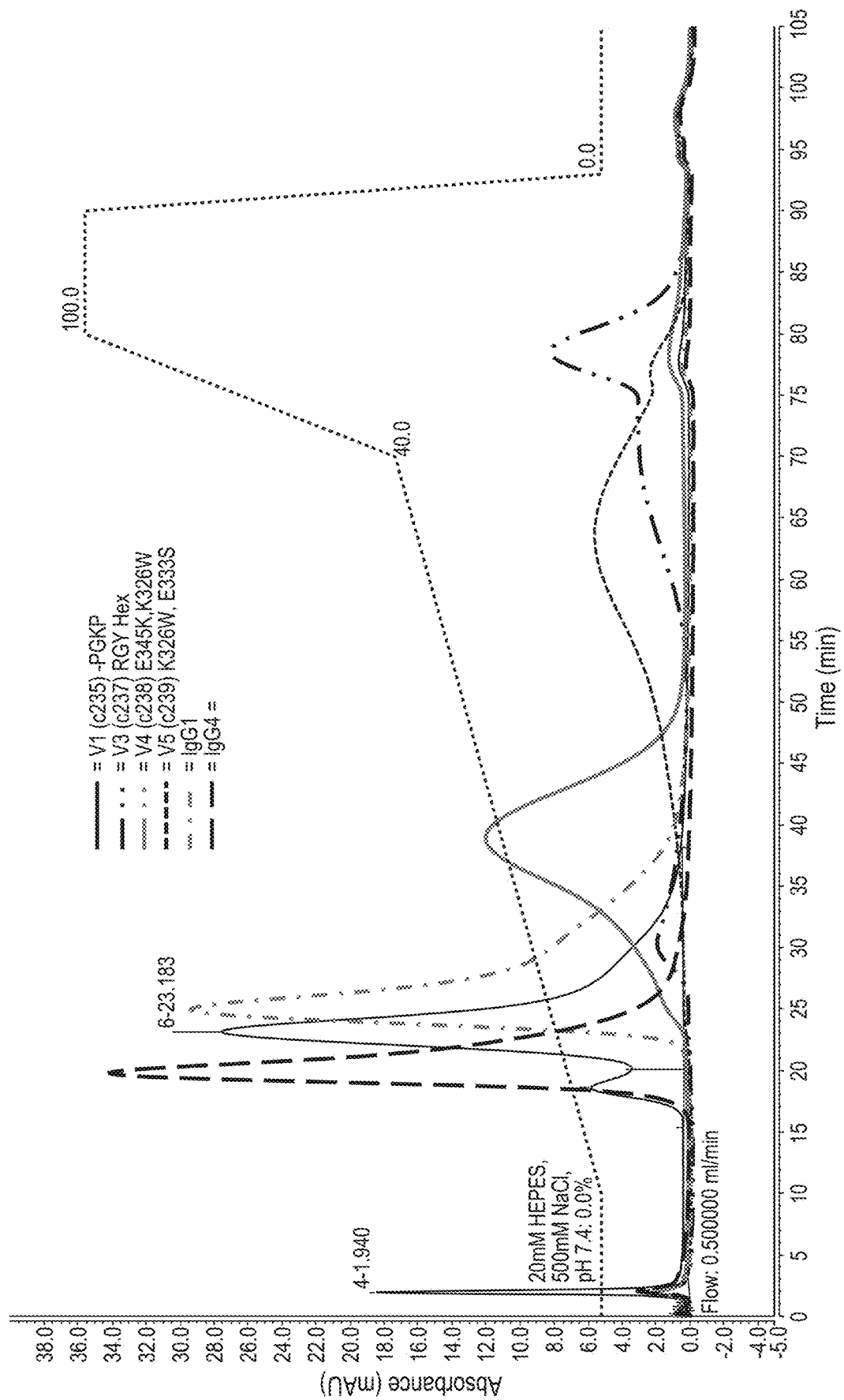
FIG. 19 Overlay of exemplary chromatograms for elution of an antibody of the IgG1 class with differently mutated Fc-regions: V1=C-terminal lysine removed; V3=E345R, E430G, S440Y; V4=E345K, K326W; V5=K326W, E333S.

As outlined in FIG. 18 the fusion protein as reported herein can be used to separate antibody Fab fragments from Fc-regions after enzymatic cleavage for further analysis.

1. Antibody Fragments

In certain embodiments, an antibody as used in the methods reported herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Pluckthun, A., In: The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Antibody fragments can be made by various techniques, including but not limited to proteolytic digestion of an intact antibody as well as production by recombinant host cells (e.g. *E. coli* or phage), as described herein.

2. Chimeric and Humanized Antibodies

In certain embodiments, an antibody as used in the methods reported herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing SDR (a-CDR) grafting); Padlan, E. A., Mol. Immunol. 28 (1991) 489-498 (describing "resurfacing"); Dall' Acqua, W. F., et al., Methods 36 (2005) 43-60 (describing "FR shuffling"); and Osbourn, J., et al., Methods 36 (2005) 61-68 and Klimka, A., et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M., et al., J. Biol. Chem. 272 (1997) 10678-10684 and Rosok, M. J., et al., J. Biol. Chem. 271 (1996) 22611-22618).

3. Human Antibodies

In certain embodiments, an antibody as used in the methods reported herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boemer, P., et al., J. Immunol. 147 (1991) 86-95) Human antibodies generated via human B-cell hybridomra technology are also described in Li, J., et al., Proc. Nal. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Antibodies used in the methods as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R., et al., Methods in Molecular Biology 178 (2002) 1-37 and further described, e.g., in the McCafferty, J., et al., Nature 348 (1990) 552-554; Clackson, T., et al., Nature 352 (1991) 624-628; Marks, J. D., et al., J. Mol. Biol. 222 (1992) 581-597; Marks, J. D. and Bradbury, A., Methods in Molecular Biology 248 (2003) 161-175; Sidhu, S. S., et al., J. Mol. Biol. 338 (2004) 299-310; Lee, C. V., et al., J. Mol. Biol. 340 (2004) 1073-1093; Fellouse, F. A., Proc. Natl. Acad. Sci. USA 101 (2004) 12467-12472; and Lee, C. V., et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, an antibody as used in the methods reported herein is a multispecific antibody, e.g. a bispecific antibody. Multispecific antibodies are monoclonal antibodies that have binding specificities for at least two different sites. In certain embodiments, bispecific antibodies may bind to two different epitopes of the same antigen. Bispecific antibodies may also be used to localize cytotoxic agents to cells which express the antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (sFv) dimers (see, e.g. Gruber, M., et al., J. Immunol. 152 (1994) 5368-5374); and preparing trispecific antibodies as described, e.g., in Tutt, A., et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to different antigens (see, US 2008/0069820, for example).

The antibody or fragment herein also includes multispecific antibodies described in WO 2009/080251, WO 2009/080252, WO 2009/080253, WO 2009/080254, WO2010/112193, WO2010/115589, WO2010/136172, WO2010/145792, and WO 2010/145793.

6. Antibody Variants

In certain embodiments, amino acid sequence variants of an antibody are contemplated and analyzed. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are used in the method as reported herein. Sites of interest for substitutional mutagenesis include the HVRs and FRs. Exemplary changes are provided in Table 1 under the heading of "exemplary substitutions", and as further described below in reference to amino acid side chain classes. Conservative substitutions are shown in Table 1 under the heading of "preferred substitutions". Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region (HVR) residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R., et al., in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation variants

In certain embodiments, an antibody used in the method as reported herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are used having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A., et al., J. Mol. Biol. 336 (2004) 1239-1249; Yamane-Ohnuki, N., et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibodies variants that can be used in the methods as reported herein may have bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region can also be used in the methods as reported herein. Such antibody variants may have improved CDC function. Such antibody variants are described, e.g., in WO 1997/30087; WO 1998/58964; and WO 1999/22764.

c) Fc region variants

In certain embodiments, one or more amino acid modifications may be introduced into the Fc-region of an antibody used in the methods reported herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the an antibody variant that possesses some but not all effector functions, which make it a desirable candidate for applications in which the half-life of the antibody in vivo is important yet certain effector functions (such as complement and ADCC) are unnecessary or deleterious is used in the methods as reported herein. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I., et al., Proc. Natl. Acad. Sci. USA 83 (1986) 7059-7063; and Hellstrom, I., et al., Proc. Natl. Acad. Sci. USA 82 (1985) 1499-1502); U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R., et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H., et al., J. Immunol. Methods 202 (1996) 163-171; Cragg, M. S., et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B., et al., Int. Immunol. 18 (2006) 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L., et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E., et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L., et al., J. Immunol. 117 (1976) 587-593, and Kim, J. K., et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 252, 253, 254, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs", in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody used in the methods as reported herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propylene glycol homopolymers, prolylpropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation can be used in the methods as reported herein. In one embodiment, the non-proteinaceous moiety is a carbon nanotube (Kam, N. W., et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

III. Recombinant Methods and Compositions

Methods for producing monoclonal antibodies have been reported first by Kohler and Milstein (Nature 256 (1975) 495-497). Thereafter the production of recombinant antibodies with myeloma cells by stably introducing the antibody-encoding nucleic acid (DNA) has been reported (see Ochi, et al., Proc. Natl. Acad. Sci. USA 80 (1983) 6351-6355).

The encoding nucleic acid of antibodies (either for the complete antibody or for the variable domains) can be isolated and sequenced using conventional procedures from an antibody producing cell. After isolation the encoding nucleic acid can be placed into one or more expression vectors. If only the encoding nucleic acid of the variable domain is isolated the expression vector comprises also a nucleic acid encoding the heavy chain and/or light chain constant region, respectively (see e.g. U.S. Pat. No. 5,658,570). The expression vector can be transfected into prokaryotic (*E. coli*) or eukaryotic host cells (CHO, HEK, BHK, SP2/0) that do not otherwise secrete antibodies.

If the encoding nucleic acid is derived from a display library, such as a phage display library, a yeast display library, or generally cell surface display library, it can be cloned directly into the expression vector.

Antibodies may be produced using recombinant methods and compositions, e.g., as described in U.S. Pat. No. 4,816,567.

For recombinant production of an antibody nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, T. U., Nat. Biotech. 22 (2004) 1409-1414; and Li, H., et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR-CHO cells (Urlaub, G., et al., Proc. Natl. Acad. Sci. USA 77 (1980) 4216-4220); and myeloma cell lines such as YO, NSO and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

IV. Immunoconjugates

In the methods of the invention also immunoconjugates comprising an antibody conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes, can be used.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M., et al., Cancer Res. 53 (1993) 3336-3342; and Lode, H. N., et al., Cancer Res. 58 (1998) 2925-2928); an anthracycline such as daunomycin or doxorubicin (see Kratz, F., et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, Phytolaca americana proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V., et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The following examples, figures and sequences are provided to aid the understanding of the present invention, the true scope of which is set forth in the appended claims.

It is understood that modifications can be made in the procedures set forth without departing from the spirit of the invention.

EXAMPLES

Methods

Electrospray Ionization Mass Spectrometry (ESI-MS)

Protein aliquots (50 rig) were deglycosylated by adding 0.5 µL N-Glycanase plus (Roche) and sodium phosphate buffer (0.1 M, pH 7.1) to obtain a final sample volume of 115 µL. The mixture was incubated at 37° C. for 18 h. Afterwards for reduction and denaturing 60 µL 0.5 M TCEP (Pierce) in 4 M guanidine*HCl (Pierce) and 50 µL 8 M guanidine*HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 µs; Pre Puls Storage, 10 µs; scan range m/z 600 to 2000. For data evaluation in-house developed software (MassAnalyzer) was used.

FcRn surface plasmon resonance (SPR) analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and thus the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05% Tween20 pH 6.0 (GE Healthcare Bioscience) as running and dilution buffer. 200 nM of native or oxidized antibody samples were injected at a flow rate of 50 µL/min at room temperature. Association time was 180 s, dissociation phase took 360 s. Regeneration of the chip surface was reached by a short injection of HBS-P, pH 8.0. Evaluation of SPR-data was performed by comparison of the biological response signal height at 180 s after injection and at 300 s after injection. The corresponding parameters are the RU max level (180 s after injection) and late stability (300 s after end of injection).

Example 1

Expression of Single Chain C1q Fusion Polypeptide

The clarified supernatants containing hexahis-tagged polypeptides were loaded on a Ni-NTA affinity chromatography resin (Qiagen, Hanbrechtikon, Switzerland) at 4° C. After wash steps each with 20 mM sodium phosphate buffer comprising 300 mM NaCl at pH 7.4 and containing 20 mM imidazole, polypeptides were eluted at a flow rate of 3 ml/min using batch elution with the same buffer containing 100 mM respectively 300 mM imidazole on an AKTA Explorer 100 chromatography system (GE Healthcare Life Sciences, Uppsala, Sweden). Fractions were pooled according to CE-SDS (LabChip GX, Caliper) under denaturing and reducing conditions, concentrated using Amicon Ultra-15 (Merck Millipore) and dialyzed against 50 mM sodium phosphate buffer containing 500 mM NaCl adjusted to pH 7.4. Purified polypeptides were quantified using a Nanodrop spectrophotometer (Nanodrop Technologies, Wilmington, Del.), analyzed by CE-SDS (LabChip GX, Caliper) and stored at −80° C.

Example 2

Preparation of C1q Affinity Column

Single chain C1q fusion polypeptide with an Avi Tag in 2 mM MOPS buffer comprising 125 mM NaCl and 0.02% Tween, adjusted to pH 7.2, and supplemented with 1 tablet Complete protease inhibitor (cOmplete ULTRA Tablets, Roche Diagnostics GmbH, Mannheim, Germany) in 3 ml PBS was biotinylated using the biotinylation kit from Avidity according to the manufacturer instructions (Bulk BIRA, Avidity LLC, Denver, Colo., USA). Biotinylation reaction was done at room temperature overnight. To separate the ligase Ni-Sepharose chromatography (see above) was repeated. The modified polypeptide was dialyzed against 50 mM sodium phosphate buffer comprising 500 mM NaCl, pH 7.2 at 4° C. overnight to remove imidazole.

One gram streptavidin sepharose (GE Healthcare) was added to the biotinylated and dialyzed polypeptide (for standard analytical applications 3 mg of C1q were chosen) and incubated for two hours with shaking. The receptor derivatized sepharose was filled in a 1 ml Tricom 5/50 column (GE Healthcare).

Example 3

Chromatography Using the C1q Affinity Column

The receptor derivatized sepharose was filled in a 1 ml Tricom 5/50 column (GE Healthcare) and the C1q column then was equilibrated with 20 mM HEPES, pH 7.4
Conditions:
column dimensions: 50 mm×5 mm
bed height: 50 mm
loading: 30 μg protein/sample
flow: 0.5 ml/min
equilibration buffer: 20 mM HEPES, pH 7.4
elution buffer: 20 mM HEPES, 500 mM NaCl, pH 7.4
elution: 10 CV equilibration buffer, in 30 CV to 40% elution buffer, 5 CV to 100% elution buffer Samples containing 30 μg of analyte (antibody or Fc-region comprising fusion polypeptide) were adjusted to pH 5.5 and applied to the C1q column using HPLC-System 10 ADVP (Shimadzu, Duisburg, Germany) or Ultimate 3000 (Thermo Fisher Scientific, Dreieich, Germany). The column with 50 mm bed height was then washed with 5-10 column volumes of equilibration buffer (20 mM HEPES, pH 7.4). The affinity-bound analyte was eluted with a salt gradient to 20 mM HEPES, 500 mM NaCl, pH 7.4 (elution buffer), within 30 column volumes. For complete elution, the salt concentration was increased in the gradient up to 100% elution buffer. The experiments were carried out at room temperature. The elution profile was obtained by continuous measurement of the absorbance at 280 nm. The time taken for an analyte peak, X, to reach the detector after sample injection was called the retention time.

Example 4

SPR Assay Using C1q

The binding properties of wild-type antibody and the mutants to C1q were analyzed by surface plasmon resonance (SPR) technology using a BIAcore T200 instrument (BIAcore AB, Uppsala, Sweden).

This system is well established for the study of molecular interactions. It allows a continuous real-time monitoring of ligand/analyte bindings and thus the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the C1q molecule was immobilized onto a BIAcore biosensor chip (GE Healthcare Bioscience, Uppsala, Sweden) via the Biotin CAPture reagent. C1q has been coupled to a level of 6000 Response units (RU). The assay was carried out at room temperature with PBS, 0.05% Tween20 pH 6.0 (GE Healthcare Bioscience) as running and dilution buffer.

Samples were injected at a flow rate of 50 μL/min at room temperature. Association time was 100 s, dissociation phase took 240 s. Regeneration was been performed by the suppliers regeneration kit of the Biotin Capture Kit. Evaluation of SPR-data was performed by comparison of the biological response signal height at 100 s after injection. The corresponding parameters are the RU level (100 s after injection).

Figure 6:
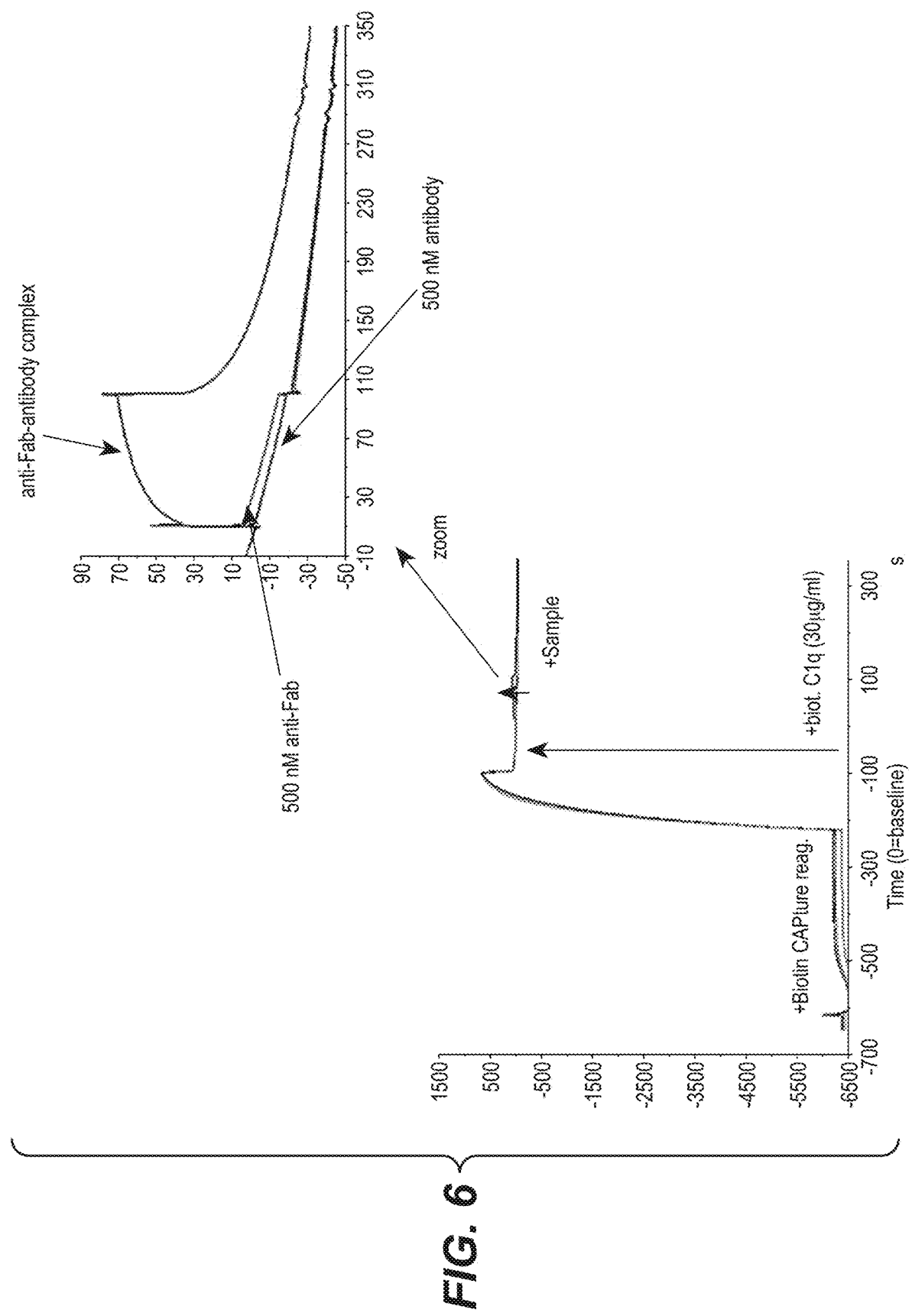

As samples wt-IgG1 antibody (500 nM) and anti-idiotypic Fab-complexed antibody were used. The respective sensogram is shown in FIG. 6. It can be seen that with the C1q ligand as used herein the binding of Fab-complex IgG is possible.

The invention claimed is:

1. A fusion polypeptide according to formula I

TAG-X1-C1qA-X2-C1qB-X3-C1qC-X4      (formula I)

wherein
    X1 denotes a first peptidic linker, X2 denotes a second peptidic linker, X3 denotes a third peptidic linker, X4 denotes a fourth peptidic linker,
    X1, X2, X3, X4 are independently of each other either present or absent, TAG is an amino acid sequence tag, TAG can be present or absent,
    C1qA has the amino acid sequence of SEQ ID NO: 07 is a fragment of SEQ ID NO: 01, C1qB has the amino acid sequence of SEQ ID NO: 08 is a fragment of SEQ ID NO: 03, C1qC has the amino acid sequence of SEQ ID NO: 09 is a fragment of SEQ ID NO: 05, and
    - denotes a peptide bond.

2. The fusion polypeptide according to claim 1, wherein X1, X2 and X3 are present and X4 is absent or wherein X2, X3 and X4 are present and X1 is absent.

3. The fusion polypeptide according to claim 1, wherein X1 has the amino acid sequence of SEQ ID NO: 10, X2 has the amino acid sequence of SEQ ID NO: 11 or 12, and X3 has the amino acid sequence of SEQ ID NO: 13 or 14, or wherein X2 has the amino acid sequence of SEQ ID NO: 13 or 14, X3 has the amino acid sequence of SEQ ID NO: 11 or 12 and X4 has the amino acid sequence of SEQ ID NO: 10.

4. The fusion polypeptide according to claim 1, wherein TAG is present and has the amino acid sequence of SEQ ID NO: 15.

5. A multimeric non-covalent complex comprising 2 to 6 fusion polypeptides according to claim 1.

6. The multimeric non-covalent complex according to claim 5, wherein in at least one of the fusion polypeptides TAG is present and in at least one of the fusion polypeptides TAG is absent.

7. An affinity chromatography ligand comprising the fusion polypeptide according to claim 1.

8. The affinity chromatography ligand according to claim 7, wherein the fusion polypeptide or the complex is immobilized on a solid phase.

9. The affinity chromatography ligand according to claim 8, wherein the solid phase is a chromatography material.

10. An affinity chromatography ligand comprising the multimeric non-covalent complex according to claim 5.

11. The affinity chromatography ligand according to claim 10, wherein the complex is immobilized on a solid phase.

12. The affinity chromatography ligand according to claim 11, wherein the solid phase is a chromatography material.

* * * * *